United States Patent
Saitoh et al.

(10) Patent No.: US 9,414,998 B2
(45) Date of Patent: Aug. 16, 2016

(54) PREVENTING OR AMELIORATING AGENT FOR PIGMENTATION

(71) Applicant: Pola Chemical Industries Inc., Shizuoka-shi, Shizuoka (JP)

(72) Inventors: Yuko Saitoh, Yokohama (JP); Chihiro Kondo, Yokohama (JP); Takashi Yamasaki, Yokohama (JP)

(73) Assignee: POLA CHEMICAL INDUSTRIES INC., Shizuoka (JP)

( * ) Notice: Subject to any disclaimer, the term of this patent is extended or adjusted under 35 U.S.C. 154(b) by 37 days.

(21) Appl. No.: 14/325,724

(22) Filed: Jul. 8, 2014

(65) Prior Publication Data

US 2014/0322150 A1 Oct. 30, 2014

Related U.S. Application Data

(62) Division of application No. 13/516,170, filed as application No. PCT/JP2010/072689 on Dec. 16, 2010, now abandoned.

(30) Foreign Application Priority Data

Dec. 16, 2009 (JP) ................................. 2009-285001

(51) Int. Cl.
| | | |
|---|---|---|
| A61K 8/44 | (2006.01) | |
| A61K 31/198 | (2006.01) | |
| A61Q 19/02 | (2006.01) | |
| C07C 233/63 | (2006.01) | |
| C07C 233/83 | (2006.01) | |
| C07C 235/52 | (2006.01) | |
| A61K 31/223 | (2006.01) | |

(52) U.S. Cl.
CPC . *A61K 8/44* (2013.01); *A61K 8/442* (2013.01); *A61K 31/198* (2013.01); *A61K 31/223* (2013.01); *A61Q 19/02* (2013.01); *C07C 233/63* (2013.01); *C07C 233/83* (2013.01); *C07C 235/52* (2013.01)

(58) Field of Classification Search
CPC ..... A61K 8/442; A61K 31/198; A61Q 19/02; C07C 233/83
USPC ........................................................ 424/42
See application file for complete search history.

(56) References Cited

U.S. PATENT DOCUMENTS

| | | | |
|---|---|---|---|
| 5,316,767 A | 5/1994 | Hara et al. | |
| 6,238,655 B1 | 5/2001 | Slife et al. | |
| 2006/0106102 A1 | 5/2006 | Morand et al. | |
| 2006/0154977 A1 | 7/2006 | Morand et al. | |
| 2006/0166901 A1 | 7/2006 | Yu et al. | |
| 2006/0287536 A1 | 12/2006 | Dahnke et al. | |
| 2007/0021473 A1 | 1/2007 | Biadatti et al. | |
| 2007/0173500 A1 | 7/2007 | Guo et al. | |
| 2007/0173501 A1 | 7/2007 | Guo et al. | |
| 2010/0168468 A1 | 7/2010 | Tsunenaga et al. | |
| 2010/0323999 A1 | 12/2010 | Morand et al. | |
| 2013/0123259 A1 | 5/2013 | Guo et al. | |
| 2013/0217650 A1 | 8/2013 | Guo et al. | |

FOREIGN PATENT DOCUMENTS

| | | |
|---|---|---|
| EP | 0919226 | 6/1999 |
| JP | 05-301811 | 11/1993 |
| JP | 06-256156 | 9/1994 |
| JP | 10-298151 | 11/1998 |
| JP | 11-049630 | 2/1999 |
| JP | 11-310510 | 11/1999 |
| JP | 2002-508307 | 3/2000 |
| JP | 2001-247443 | 9/2001 |
| JP | 2002-087928 | 3/2002 |
| JP | 2002-173473 | 6/2002 |
| JP | 2004-115438 | 4/2004 |
| JP | 2006-327972 | 12/2006 |
| WO | WO 98/35982 | 8/1998 |
| WO | WO 03/091211 | 11/2003 |
| WO | WO 03/101978 A1 | 12/2003 |
| WO | WO 03/104203 A1 | 12/2003 |
| WO | WO 2005/056516 A1 | 6/2005 |
| WO | WO 2006/044775 | 4/2006 |
| WO | WO 2006/074114 A2 | 7/2006 |
| WO | WO 2007/013662 | 2/2007 |
| WO | WO 2007/087419 A2 | 8/2007 |
| WO | WO 2008/028937 | 3/2008 |

OTHER PUBLICATIONS

Costin et al.; Title:Human skin pigmentation: melanocytes modulate skin color in response to stress; The FASEB Journal vol. 21 No. 4, pp. 976-994, published Jan. 22, 2007.*

(Continued)

*Primary Examiner* — Ali Soroush
*Assistant Examiner* — Yanzhi Zhang
(74) *Attorney, Agent, or Firm* — Knobbe, Martens, Olson & Bear, LLP

(57) ABSTRACT

An external preparation for skin is provided for amelioration of pigmentation. The skin preparation includes a compound represented by the following general formula (1), an isomer thereof, and/or a pharmacologically acceptable salt thereof:

$$\underset{R_1}{\underset{\|}{\overset{O}{C}}}-\underset{H}{\overset{}{N}}-\underset{}{\overset{}{C}}H(CH_2OR_2)-\underset{}{\overset{\|}{\underset{O}{C}}}-OR_3$$

wherein $R_1$ represents an aromatic group; $R_2$ represents a hydrogen atom, or a linear or branched chain alkyl or acyl group having 1 to 4 carbon atoms; and $R_3$ represents a hydrogen atom or a linear chain or branched chain alkyl group having 1 to 4 carbon atoms.

6 Claims, No Drawings

(56) References Cited

OTHER PUBLICATIONS

Helfrich et al; title: Overview of skin aging and photoaging; Dermatology nursing/Dermatology Nurses' Association, vol. 20 (3), pp. 177-183, Jun. 2008 issue).*

International Search Report dated Mar. 8, 2011, issued to international application No. PCT/JP2010/072689.

Omori, Takayuki, Fragrance Journal, extra (special) issue, No. 14, pp. 118-126, 1995.

Schnabelrauch, et al. "New Synthetic Catecholate-type Siderophores Based on Amino Acids and Dipeptides," *BioMetals*, vol. 13, pp. 333-348, 2000.

Takeda, Katsuhiko, "Usefulness of Cosmetics, Evaluation Techniques and future Overview," published by Yakuji Nippo Limited, pp. 149-151, 2001.

Extended European Search Report for corresponding European Patent Application No. 10837668.2, dated Apr. 28, 2014.

Office Action issued in Australian Patent Application No. 2010331250 on Nov. 13, 2014.

* cited by examiner

PREVENTING OR AMELIORATING AGENT FOR PIGMENTATION

CROSS-REFERENCE TO RELATED APPLICATIONS

This application is a divisional of U.S. application Ser. No. 13/516,170, filed Jun. 14, 2012 which is the U.S. National Phase under 35 U.S.C. §371 of International Application PCT/JP2010/072689, filed Dec. 16, 2010, which was published in a non-English language, which claims priority to JP Application No.: 2009-285001, filed Dec. 16, 2009.

TECHNICAL FIELD

The present invention relates to an external preparation for skin which is preferably usable for cosmetic preparations (including quasi-pharmaceutical products or quasi-drugs). In particular, the present invention relates to a prophylactic (preventing) or ameliorating agent for pigmentation which consists of a compound represented by the following general formula (1), an isomer thereof, and/or a pharmacologically acceptable salt thereof, and an external preparation for skin which contains the same as a component.

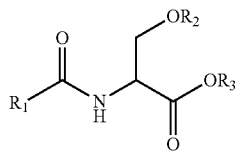

(1)

[wherein $R_1$ represents an unsubstituted aromatic group or an aromatic group having any substituent, $R_2$ represents a hydrogen atom, a linear chain or branched chain alkyl group having a number of carbon atom or atoms of 1 to 4, or an acyl group having a linear or branched alkyl chain having a number of carbon atom or atoms of 1 to 4, and $R_3$ represents a hydrogen atom or a linear chain or branched chain alkyl group having a number of carbon atom or atoms of 1 to 4.]

BACKGROUND ART

For example, the pigmentation which are caused on the skin after the suntan or sunburn, the freckle, the chloasma, and the senile pigment freckle, reside in such a state that the melanin production is extremely facilitated or enhanced on account of the activation of the pigment cell (melanocyte) existing in the skin. The component, which is well-known to have the function for preventing or ameliorating the occurrence and the deterioration of the skin pigment trouble as described above, is the compound (skin whitening agent) having the skin whitening function including, for example, ascorbic acid and its derivatives, hydrogen peroxide, colloidal sulfur, glutathione, hydroquinone, and catechol (see, for example, Non-Patent Document 1 and Non-Patent Document 2). External preparations for skin, which are blended with the components as described above as the active ingredients, are widely used. At present, a variety of mechanisms of action, including, for example, the tyrosinase enzyme inhibiting action, the tyrosinase-related protein degradation, and the melanin transfer inhibition caused by the suppression of dendrite elongation in melanocyte have been reported as the mechanism of action exhibited by the compound known as the skin whitening agent. Target molecules are present with respect to the respective mechanisms of action. In order to appropriately exert the action on the target molecule and express the high skin whitening effect, an organic low molecular weight compound, which appropriately interacts with the target molecule, is useful. Further, the organic low molecular weight compound, which appropriately interacts with each of the target molecules, has the structural properties which differs depending on each of the target molecules. Therefore, studies are vigorously performed as well in relation to the optimization of the chemical structure in order to maximally make the use of the pharmacological action exhibited by the organic low molecular weight compound. Further, at present, studies on the skin whitening agent are not limited to the compound which has the high efficacy and the high selectivity with respect to the existing target molecule, and studies are widened, for example, to the compound which simultaneously acts on a plurality of skin whitening target molecules and the compound which has a novel mechanism of action. The excellent skin whitening function is expected for such skin whitening agent. Actually, the screening has been carried out in relation to compounds having excellent skin whitening functions to seek for useful compounds which have various chemical structures or pharmacological characteristics. Any skin whitening agent, which has a novel scaffold nucleus, is still demanded even now.

Amino acid is the general term of organic compounds having both functional groups of amino group and carboxyl group in each of molecules thereof. In particular, studies are vigorously made about α-amino acid as the constitutive unit of protein to express various functions in the living body. Various physiological activities have been reported for α-amino acids including, for example, cysteine, arginine, valine, threonine, serine, and glycine existing in the living body as well as peptide derivatives including α-amino acids as constitutive elements. Even in the case of only the field of the cosmetics, the biological activities, which are known to be possessed by α-amino acids and derivatives thereof, include the actions of, for example, the antiaging action (see, for example, Patent Document 1), the moistening action (see, for example, Patent Document 2), the skin whitening action (see, for example, Patent Document 3), and the surface activating action. α-Amino acids and derivatives thereof are blended, for example, in cosmetic preparations in order to obtain the effects thereof. In general, the amino acids and the derivatives thereof as described above are excellent in the solubility, especially in the water solubility in addition to the efficacy, and the high safety is expected as well. Therefore, the blending in the cosmetic or the like is vigorously studied. However, it is hardly affirmed that the biological activities of, for example, the antiaging action, the moistening action, or the skin whitening action, which are possessed by α-amino acids and derivatives thereof as described above, are sufficiently efficacious. Studies are continuously made in relation to α-amino acids and derivatives thereof in order to enhance the biological activity. According to a study in relation to a serine derivative of amino acids and derivatives thereof as described above, it is known that N-methylserine has the moistening action (see, for example, Patent Document 4), the rough skin ameliorating effect and the wrinkle decreasing effect (see, for example, Patent Document 5), and the action to enhance the melanin production suppressing action of glabridin (see, for example, Patent Document 6). Further, it is known that N-benzoylserine has the moistening action (see, for example, Patent Document 7) and the wrinkle preventing or ameliorating action (see, for example, Patent Document 8). However, any skin whitening effect has not been clarified in relation to the serine derivatives as described above. It has not been known at all that the compound represented by the general formula (1) described above, the isomer thereof, and/or the pharmacologically acceptable salt thereof has/have the prophylactic or ameliorating action for preventing or ameliorating the pigmentation.

PRIOR ART DOCUMENTS

Patent Documents

Patent Document 1: JP2004-115438A;
Patent Document 2: JP2002-087928A;
Patent Document 3: JP05-301811A;
Patent Document 4: JP11-310510A;
Patent Document 5: JP2001-247443A;
Patent Document 6: JP06-256156A;
Patent Document 7: JP2006-327972A;
Patent Document 8: WO2007/013662.

Non-Patent Documents

Non-Patent Document 1: "Usefulness of Cosmetics, Evaluation Techniques and Future Overview", supervised by Katsuyuki TAKEDA, published by YAKUJI NIPPO LIMITED (2001);
Non-Patent Document 2: Takayuki Omori, FRAGRANCE JOURNAL, extra (special) issue, No. 14, 1995, 118-126.

SUMMARY OF THE INVENTION

The present invention has been made under the circumstances as described above, with the object of providing an external preparation for skin that is preferably usable to prevent or ameliorate (improve) pigmentation.

Taking the foregoing circumstances into consideration, the present inventors have repeatedly made vigorous efforts while seeking for a novel prophylactic or ameliorating agent for pigmentation preferably usable for a cosmetic preparation (provided that the cosmetic preparation includes quasi-pharmaceutical products or quasi-drugs). As a result, it has been found out that the compound represented by the general formula (1) described above, the isomer thereof, and/or the pharmacologically acceptable salt thereof is/are excellent in the prophylactic or ameliorating action or function for preventing or ameliorating (improving) the pigmentation. Thus, the present invention has been completed. The present invention is as follows.

<1> A preventing or ameliorating agent for pigmentation, consisting of a compound represented by the following general formula (1), an isomer thereof, and/or a pharmacologically acceptable salt thereof:

$$R_1 \underset{H}{\overset{O}{\underset{\|}{\text{—C—N}}}} \overset{OR_2}{\underset{\underset{O}{\|}{\text{—C—OR}_3}}{\text{—CH—}}} \quad (1)$$

[wherein:
R₁ represents an unsubstituted aromatic group or an aromatic group having any substituent;

R₂ represents a hydrogen atom, a linear chain or branched chain alkyl group having a number of carbon atom or atoms of 1 to 4, or an acyl group having a linear or branched alkyl chain having a number of carbon atom or atoms of 1 to 4; and
R₃ represents a hydrogen atom or a linear chain or branched chain alkyl group having a number of carbon atom or atoms of 1 to 4.]

<2> The preventing or ameliorating agent for pigmentation as defined in <1>, wherein in the general formula (1);
R₁ is the unsubstituted aromatic group or the aromatic group having the substituent which is a linear chain or branched chain alkyl group having a number of carbon atom or atoms of 1 to 6, an alkoxy group having a linear or branched alkyl chain having a number of carbon atom or atoms of 1 to 6, an alkylamino group having a linear or branched alkyl chain or chains having a number of carbon atom or atoms of 1 to 6, an acyl group having a linear or branched alkyl chain having a number of carbon atom or atoms of 1 to 6, an ester group having a linear or branched alkyl chain having a number of carbon atom or atoms of 1 to 6, a halogen atom, a halogenated alkyl group, a hydroxy group, or an amino group;
R₂ is a hydrogen atom, a methyl group, an ethyl group, an n-propyl group, an isopropyl group, an n-butyl group, an isobutyl group, a tert-butyl group, an acetyl group, a propionyl group, or a butyryl group; and
R₃ is a hydrogen atom, a methyl group, an ethyl group, an n-propyl group, an isopropyl group, an n-butyl group, an isobutyl group, or a tert-butyl group.

<3> The preventing or ameliorating agent for pigmentation as defined in <2>, wherein in the general formula (1);
R₁ is an unsubstituted phenyl, naphthyl, or biphenyl group or a phenyl, naphthyl, or biphenyl group having the substituent which is a linear chain or branched chain alkyl group having a number of carbon atom or atoms of 1 to 6, an alkoxy group having a linear or branched alkyl chain having a number of carbon atom or atoms of 1 to 6, an alkylamino group having a linear or branched alkyl chain or chains having a number of carbon atom or atoms of 1 to 6, an acyl group having a linear or branched alkyl chain having a number of carbon atom or atoms of 1 to 6, an ester group having a linear or branched alkyl chain having a number of carbon atom or atoms of 1 to 6, a halogen atom, a halogenated alkyl group, a hydroxy group, or an amino group;
R₂ is a hydrogen atom, a methyl group, or an acetyl group; and
R₃ is a hydrogen atom, a methyl group, or an ethyl group.

<4> The preventing or ameliorating agent for pigmentation as defined in any one of <1> to <3>, wherein the compound represented by the general formula (1) is N-benzoyl-serine (Compound 2), N-(p-methylbenzoyl)serine (Compounds 1, 3, 15), N-(p-ethylbenzoyl)serine (Compound 7), N-(p-methoxybenzoyl)serine (Compound 5), N-(p-fluorobenzoyl) serine (Compound 4), N-(p-trifluoromethylbenzoyl)serine (Compound 8), N-(2-naphthoyl)serine (Compound 10), N-(4-phenylbenzoyl)serine (Compound 14), N-(p-methylbenzoyl)serine methyl ester (Compound 6), N-(p-methylbenzoyl)serine ethyl ester (Compound 17), N-(2-naphthoyl) serine methyl ester (Compound 12), N-benzoyl-O-methylserine (Compound 16), N-(p-methylbenzoyl)-O-methylserine (Compound 9), N-(p-methylbenzoyl)-O-acetylserine (Compound 11), N-(2-naphthoyl)-O-methylserine (Compound 13), an isomer thereof, and/or a pharmacologically acceptable salt thereof.

<5> A preventing or ameliorating agent for pigmentation, consisting of a compound represented by the following general formula (2), an isomer thereof, and/or a pharmacologically acceptable salt thereof:

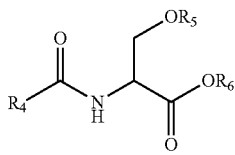

(2)

[wherein:

$R_4$ represents an unsubstituted aromatic group or an aromatic group having any substituent (provided that unsubstituted phenyl group is excluded);

$R_5$ represents a hydrogen atom, a linear chain or branched chain alkyl group having a number of carbon atom or atoms of 1 to 4, or an acyl group having a linear or branched alkyl chain having a number of carbon atom or atoms of 1 to 4;

$R_6$ represents a hydrogen atom or a linear chain or branched chain alkyl group having a number of carbon atom or atoms of 1 to 4; and at least one of $R_5$ and $R_6$ is any group other than the hydrogen atom when $R_4$ is a phenyl group having any substituent or an unsubstituted naphthyl group.]

<6> The preventing or ameliorating agent for pigmentation as defined in <5>, wherein in the general formula (2);

$R_4$ is the unsubstituted aromatic group or the aromatic group having the substituent which is a linear chain or branched chain alkyl group having a number of carbon atom or atoms of 1 to 6, an alkoxy group having a linear or branched alkyl chain having a number of carbon atom or atoms of 1 to 6, an alkylamino group having a linear or branched alkyl chain or chains having a number of carbon atom or atoms of 1 to 6, an acyl group having a linear or branched alkyl chain having a number of carbon atom or atoms of 1 to 6, an ester group having a linear or branched alkyl chain having a number of carbon atom or atoms of 1 to 6, a halogen atom, a halogenated alkyl group, a hydroxy group, or an amino group (provided that unsubstituted phenyl group is excluded);

$R_5$ is a hydrogen atom, a methyl group, an ethyl group, an n-propyl group, an isopropyl group, an n-butyl group, an isobutyl group, a tert-butyl group, an acetyl group, a propionyl group, or a butyryl group;

$R_6$ is a hydrogen atom, a methyl group, an ethyl group, an n-propyl group, an isopropyl group, an n-butyl group, an isobutyl group, or a tert-butyl group; and at least one of $R_5$ and $R_6$ is any group other than the hydrogen atom when $R_4$ is the phenyl group having the substituent or the unsubstituted naphthyl group.

<7> The preventing or ameliorating agent for pigmentation as defined in <6>, wherein in the general formula (2);

$R_4$ is a phenyl group having the substituent which is a linear chain or branched chain alkyl group having a number of carbon atom or atoms of 1 to 6, an alkoxy group having a linear or branched alkyl chain having a number of carbon atom or atoms of 1 to 6, an alkylamino group having a linear or branched alkyl chain or chains having a number of carbon atom or atoms of 1 to 6, an acyl group having a linear or branched alkyl chain having a number of carbon atom or atoms of 1 to 6, an ester group having a linear or branched alkyl chain having a number of carbon atom or atoms of 1 to 6, a halogen atom, a halogenated alkyl group, a hydroxy group, or an amino group, an unsubstituted naphthyl or biphenyl group, or a naphthyl or biphenyl group having the substituent as defined above;

$R_5$ is a hydrogen atom, a methyl group, or an acetyl group;

$R_6$ is a hydrogen atom, a methyl group, or an ethyl group; and at least one of $R_5$ and $R_6$ is any group other than the hydrogen atom when $R_4$ is the phenyl group having the substituent or the unsubstituted naphthyl group.

<8> An external preparation for skin, containing the preventing or ameliorating agent for pigmentation as defined in any one of <1> to <7>.

<9> The external preparation for skin as defined in <8>, wherein 0.0001% by mass to 20% by mass of the preventing or ameliorating agent for pigmentation is contained with respect to a total amount of the external preparation for skin.

<10> The external preparation for skin as defined in <8> or <9>, wherein the external preparation for skin is a cosmetic preparation (provided that quasi-pharmaceutical products or quasi-drugs are included).

<11> A compound represented by the following general formula (2), an isomer thereof, and/or a pharmacologically acceptable salt thereof:

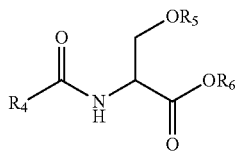

(2)

[wherein:

$R_4$ represents an unsubstituted aromatic group or an aromatic group having any substituent (provided that unsubstituted phenyl group is excluded);

$R_5$ represents a hydrogen atom, a linear chain or branched chain alkyl group having a number of carbon atom or atoms of 1 to 4, or an acyl group having a linear or branched alkyl chain having a number of carbon atom or atoms of 1 to 4;

$R_6$ represents a hydrogen atom or a linear chain or branched chain alkyl group having a number of carbon atom or atoms of 1 to 4; and at least one of $R_5$ and $R_6$ is any group other than the hydrogen atom when $R_4$ is a phenyl group having any substituent or an unsubstituted naphthyl group.]

<12> The compound as defined in <11>, wherein in the general formula (2);

$R_4$ is the unsubstituted aromatic group or the aromatic group having the substituent which is a linear chain or branched chain alkyl group having a number of carbon atom or atoms of 1 to 6, an alkoxy group having a linear or branched alkyl chain having a number of carbon atom or atoms of 1 to 6, an alkylamino group having a linear or branched alkyl chain or chains having a number of carbon atom or atoms of 1 to 6, an acyl group having a linear or branched alkyl chain having a number of carbon atom or atoms of 1 to 6, an ester group having a linear or branched alkyl chain having a number of carbon atom or atoms of 1 to 6, a halogen atom, a halogenated alkyl group, a hydroxy group, or an amino group (provided that unsubstituted phenyl group is excluded);

$R_5$ is a hydrogen atom, a methyl group, an ethyl group, an n-propyl group, an isopropyl group, an n-butyl group, an isobutyl group, a tert-butyl group, an acetyl group, a propionyl group, or a butyryl group;

$R_6$ is a hydrogen atom, a methyl group, an ethyl group, an n-propyl group, an isopropyl group, an n-butyl group, an isobutyl group, or a tert-butyl group; and at least one of $R_5$ and $R_6$ is any group other than the hydrogen atom when $R_4$ is the phenyl group having the substituent or the unsubstituted naphthyl group.

<13> The compound as defined in <12>, wherein in the general formula (2);

$R_4$ represents a phenyl group having the substituent which is a linear chain or branched chain alkyl group having a number of carbon atom or atoms of 1 to 6, an alkoxy group having a linear or branched alkyl chain having a number of carbon atom or atoms of 1 to 6, an alkylamino group having a linear or branched alkyl chain or chains having a number of carbon atom or atoms of 1 to 6, an acyl group having a linear or branched alkyl chain having a number of carbon atom or atoms of 1 to 6, an ester group having a linear or branched alkyl chain having a number of carbon atom or atoms of 1 to 6, a halogen atom, a halogenated alkyl group, a hydroxy group, or an amino group, an unsubstituted naphthyl or biphenyl group, or a naphthyl or biphenyl group having the substituent as defined above;

$R_5$ represents a hydrogen atom, a methyl group, or an acetyl group;

$R_6$ represents a hydrogen atom, a methyl group, or an ethyl group; and at least one of $R_5$ and $R_6$ is any group other than the hydrogen atom when $R_4$ is the phenyl group having the substituent or the unsubstituted naphthyl group.

<14> A compound represented by the general formula (1) or (2) as defined above, a compound defined in <2>, <3>, <4>, <6>, or <7> as defined above, an isomer thereof, and/or a pharmacologically acceptable salt thereof for prophylaxis or amelioration for pigmentation.

<15> A preventing or ameliorating method for pigmentation, comprising administering a compound represented by the general formula (1) or (2) as defined above, a compound defined in <2>, <3>, <4>, <6>, or <7> as defined above, an isomer thereof, and/or a pharmacologically acceptable salt thereof to an object for which prophylaxis or amelioration for pigmentation is required.

DESCRIPTION OF THE EMBODIMENTS

<Prophylactic or Ameliorating Agent for Pigmentation as Essential Component in External Preparation for Skin of the Present Invention>

The external preparation for skin of the present invention is characterized in that the external preparation for skin contains the prophylactic or ameliorating agent for pigmentation consisting of the compound represented by the general formula (1) described above, the isomer thereof, and/or the pharmacologically acceptable salt thereof. The prophylactic or ameliorating agent for pigmentation of the present invention also comprises the function to prevent the pigmentation in addition to the function to ameliorate (improve) the pigmentation in which the pigmentation, which has been already formed, is diluted or eliminated (erased). Any component is applicable to the prophylactic or ameliorating agent for pigmentation of the present invention without any special limitation, provided that the component resides in the compound represented by the general formula (1) described above, the isomer thereof, and/or the pharmacologically acceptable salt thereof, and the component has the function to prevent or ameliorate the pigmentation. However, more preferably, it is possible to appropriately exemplify the component which has the function to suppress the pigmentation in "Evaluation of function to suppress pigmentation caused by ultraviolet radiation based on use of pigmented guinea pig" as described later on. The component, which has the function to suppress the pigmentation in the evaluation of the function to suppress the pigmentation described above, means the component in which the function to suppress the pigmentation is confirmed in the group to which the substance to be evaluated is administered as compared with the control group (solvent control group). More preferably, it is appropriate to provide the component in which the statistically significant difference is confirmed in the function to suppress the pigmentation in relation to the group to which the substance to be evaluated is administered as compared with the control group.

The compound represented by the general formula (1), the isomer thereof, and/or the pharmacologically acceptable salt thereof will now be described. In the formula, $R_1$ represents an unsubstituted aromatic group or an aromatic group having any substituent; $R_2$ represents a hydrogen atom, a linear chain or branched chain alkyl group having a number of carbon atom or atoms of 1 to 4, or an acyl group having a linear or branched alkyl chain having a number of carbon atom or atoms of 1 to 4; and $R_3$ represents a hydrogen atom or a linear chain or branched chain alkyl group having a number of carbon atom or atoms of 1 to 4.

$R_1$ described above represents the unsubstituted aromatic group or the aromatic group having the substituent, and the substituent on the aromatic group can be preferably exemplified, for example, by a hydrogen atom, an alkyl group having a number of carbon atom or atoms of 1 to 6, more preferably having a number of carbon atom or atoms of 1 to 3, an alkoxy group having an alkyl chain having a number of carbon atom or atoms of 1 to 6, more preferably having a number of carbon atom or atoms of 1 to 3, an alkylamino group having an alkyl chain or chains having a number of carbon atom or atoms of 1 to 6, more preferably having a number of carbon atom or atoms of 1 to 3, an acyl group having an alkyl chain having a number of carbon atom or atoms of 1 to 6, more preferably having a number of carbon atom or atoms of 1 to 3, an ester group having an alkyl chain having a number of carbon atom or atoms of 1 to 6, more preferably having a number of carbon atom or atoms of 1 to 3, a halogen atom, a halogenated alkyl group (preferably a halogenated alkyl group having a number of carbon atom or atoms of 1 to 4), a hydroxy group, and an amino group.

Specified examples are exemplified in relation to the unsubstituted aromatic group or the aromatic group having the substituent. It is possible to preferably exemplify, for example, phenyl group, methylphenyl group, ethylphenyl group, propylphenyl group, butylphenyl group, methoxyphenyl group, ethoxyphenyl group, propyloxyphenyl group, butyloxyphenyl group, N-methylaminophenyl group, N-ethylaminophenyl group, N-propylaminophenyl group, N-butylaminophenyl group, N,N,-dimethylaminophenyl group, N,N-diethylaminophenyl group, N,N-dipropylaminophenyl group, N,N-dibutylaminophenyl group, acetylphenyl group, propionylphenyl group, butyrylphenyl group, methoxycarbonylphenyl group, ethoxycarbonylphenyl group, propyloxycarbonylphenyl group, butyloxycarbonylphenyl group, fluorophenyl group, chlorophenyl group, bromophenyl group, trifluoromethylphenyl group, hydroxyphenyl group, aminophenyl group, pyridyl group, methylpyridyl group, ethylpyridyl group, propylpyridyl group, butylpyridyl group, methoxypyridyl group, ethoxypyridyl group, propyloxypyridyl group, butyloxypyridyl group, N-methylaminopyridyl group, N-ethyaminopyridyl group, N-propylaminopyridyl group, N-butylaminopyridyl group, N,N-dimethylaminopyridyl group, N,N-diethylaminopyridyl group, N,N-dipropylaminopyridyl group, N,N-dibutylaminopyridyl group, acetylpyridyl group, propionylpyridyl group, butyrylpyridyl group, methoxycarbonypyridyl group, ethoxycarbonylpyridyl group, propyloxycarbonylpyridyl group, butyloxycarbonylpyridyl group, fluoropyridyl group, chloropyridyl group, bromopyridyl group, trifluoromethylpyridyl group, hydroxypyridyl group, aminopyridyl group, naphthyl group, methylnaphthyl group, ethylnaphthyl group, propylnaphthyl group, butylnaphthyl group, methoxynaphthyl group, ethoxynaphthyl group, propyloxynaphthyl group, butyloxynaphthyl group, N-methylaminonaphthyl group, N-ethylaminonaphthyl group, N-propylaminonaphthyl group, N-butylaminonaphthyl group, N,N-dimethylaminonaphthyl group, N,N-diethylaminonaphthyl group, N,N-dipropylaminonaphthyl group, N,N-dibutylaminonaphthyl group, acetylnaphthyl group, propionylnaphthyl group, butyrylnaphthyl group, methoxycarbonylnaphthyl group, ethoxycarbonylnaphthyl group, propyloxycarbonylnaphthyl group, butyloxycarbonylnaphthyl group, fluoronaphthyl group, chloronaphthyl group, bromonaphthyl group, trifluoromethylnaphthyl group, hydroxynaphthyl group, aminonaphthyl group, biphenyl group, methylbiphenyl group, ethylbiphenyl group, propylbiphenyl group, butylbiphenyl group, methoxybiphenyl group, ethoxybiphenyl group, propyloxybiphenyl group, butyloxybiphenyl group, N-methylaminobiphenyl group, N-ethylaminobiphenyl group, N-propylaminobiphenyl group, N-butylaminobiphenyl group, N,N-dimethylaminobiphenyl group, N,N-diethylaminobiphenyl group, N,N-dipropylaminobiphenyl group, N,N-dibutylaminobiphenyl group, acetylbiphenyl group, propionylbiphenyl group, butyrylbiphenyl group, methoxycarbonylbiphenyl group, ethoxycarbonylbiphenyl group, propyloxycarbonylbiphenyl group, butyloxycarbonylbiphenyl group, fluorobiphenyl group, chlorobiphenyl group, bromobiphenyl group, trifluoromethylbiphenyl group, hydroxybiphenyl group, and aminobiphenyl group. Among them, those preferably usable can be preferably exemplified, for example, by phenyl group, methylphenyl group, ethylphenyl group, methoxyphenyl group, ethoxyphenyl group, fluorophenyl group, trifluoromethylphenyl group, naphthyl group, and biphenyl group.

The number of the substituent or substituents of the aromatic group described above can be preferably exemplified by 0 to 3, and the number is more preferably 0 or 1. One or two or more of the substituent or substituents as described above can exist independently on the aromatic ring.

$R_2$ described above represents a hydrogen atom, a linear chain or branched chain alkyl group having a number of carbon atom or atoms of 1 to 4, or an acyl group having a linear or branched alkyl chain having a number of carbon atom or atoms of 1 to 4. Specified examples can be preferably exemplified, for example, by a hydrogen atom, a methyl group, an ethyl group, an n-propyl group, an isopropyl group, an n-butyl group, an isobutyl group, a tert-butyl group, an acetyl group, a propionyl group, and a butyryl group. More preferably, it is possible to preferably exemplify a hydrogen atom, a methyl group, and an acetyl group.

$R_3$ described above represents a hydrogen atom or a linear chain or branched chain alkyl group having a number of carbon atom or atoms of 1 to 4. Specified examples can be preferably exemplified, for example, by a hydrogen atom, a methyl group, an ethyl group, an n-propyl group, an isopropyl group, an n-butyl group, an isobutyl group, and a tert-butyl group. More preferably, it is possible to preferably exemplify a hydrogen atom, a methyl group, and an ethyl group.

Those more preferably usable as the compound represented by the general formula (1) described above can be preferably exemplified by the compound defined in <2> described above, the isomer thereof, and/or the pharmacologically acceptable salt thereof, as well as the compound represented by the general formula (2) described above, the isomer thereof, and/or the pharmacologically acceptable salt thereof.

Those preferably usable as the compound defined in <2> described above can be preferably exemplified by the compound defined in <3> described above, the isomer thereof, and/or the pharmacologically acceptable salt thereof, which can be more preferably exemplified by the compound defined in <4> described above, the isomer thereof, and/or the pharmacologically acceptable salt thereof.

Those more preferably usable as the compound represented by the general formula (2) described above can be preferably exemplified by the compound defined in <6> described above, the isomer thereof, and/or the pharmacologically acceptable salt thereof, which can be more preferably exemplified by the compound defined in <7> described above, the isomer thereof, and/or the pharmacologically acceptable salt thereof.

The compound represented by the general formula (2), the compound defined in <6> described above, the compound defined in <7> described above, the isomers thereof and/or the pharmacologically acceptable salts thereof are novel compounds.

The compound represented by the general formula (2), the isomer thereof, and/or the pharmacologically acceptable salt thereof will now be described. In the formula, $R_4$ represents an unsubstituted aromatic group or an aromatic group having any substituent (provided that unsubstituted phenyl group is excluded); $R_5$ represents a hydrogen atom, a linear chain or branched chain alkyl group having a number of carbon atom or atoms of 1 to 4, or an acyl group having a linear or branched alkyl chain having a number of carbon atom or atoms of 1 to 4; $R_6$ represents a hydrogen atom or a linear chain or branched chain alkyl group having a number of carbon atom or atoms of 1 to 4; and at least one of $R_5$ and $R_6$ is any group other than the hydrogen atom when $R_4$ is a phenyl group having any substituent or an unsubstituted naphthyl group.

$R_4$ described above represents the unsubstituted aromatic group or the aromatic group having the substituent, and the substituent on the aromatic group can be preferably exemplified, for example, by a hydrogen atom, an alkyl group having a number of carbon atom or atoms of 1 to 6, more preferably having a number of carbon atom or atoms of 1 to 3, an alkoxy group having an alkyl chain having a number of carbon atom or atoms of 1 to 6, more preferably having a number of carbon atom or atoms of 1 to 3, an alkylamino group having an alkyl chain or chains having a number of carbon atom or atoms of 1 to 6, more preferably having a number of carbon atom or atoms of 1 to 3, an acyl group having an alkyl chain having a number of carbon atom or atoms of 1 to 6, more preferably having a number of carbon atom or atoms of 1 to 3, an ester group having an alkyl chain having a number of carbon atom or atoms of 1 to 6, more preferably having a number of carbon atom or atoms of 1 to 3, a halogen atom, a halogenated alkyl group (preferably a halogenated alkyl group having a number of carbon atom or atoms of 1 to 4), a hydroxy group, and an amino group.

Specified examples are exemplified in relation to the unsubstituted aromatic group or the aromatic group having the substituent. It is possible to preferably exemplify, for example, methylphenyl group, ethylphenyl group, propylphenyl group, butylphenyl group, methoxyphenyl group, ethoxyphenyl group, propyloxyphenyl group, butyloxyphenyl group, N-methylaminophenyl group, N-ethylaminophenyl group, N-propylaminophenyl group, N-butylaminophenyl group, N,N,-dimethylaminophenyl group, N,N-diethylaminophenyl group, N,N-dipropylaminophenyl group, N,N-dibutylaminophenyl group, acetylphenyl group, propionylphenyl group, butyrylphenyl group, methoxycarbonylphenyl group, ethoxycarbonylphenyl group, propyloxycarbonylphenyl group, butyloxycarbonylphenyl group, fluorophenyl group, chlorophenyl group, bromophenyl group, trifluoromethylphenyl group, hydroxyphenyl group, aminophenyl group, pyridyl group, methylpyridyl group, ethylpyridyl group, propylpyridyl group, butylpyridyl group, methoxypyridyl group, ethoxypyridyl group, propyloxypyridyl group, butyloxypyridyl group, N-methylaminopyridyl group, N-ethyaminopyridyl group, N-propylaminopyridyl group, N-butylaminopyridyl group, N,N-dimethylaminopyridyl group, N,N-diethylaminopyridyl group, N,N-dipropylaminopyridyl group, N,N-dibutylaminopyridyl group, acetylpyridyl group, propionylpyridyl group, butyrylpyridyl group, methoxycarbonypyridyl group, ethoxycarbonylpyridyl group, propyloxycarbonylpyridyl group, butyloxycarbonylpyridyl group, fluoropyridyl group, chloropyridyl group, bromopyridyl group, trifluoromethylpyridyl group, hydroxypyridyl group, aminopyridyl group, naphthyl group, methylnaphthyl group, ethylnaphthyl group, propylnaphthyl group, butylnaphthyl group, methoxynaphthyl group, ethoxynaphthyl group, propyloxynaphthyl group, butyloxynaphthyl group, N-methylaminonaphthyl group, N-ethylaminonaphthyl group, N-propylaminonaphthyl group, N-butylaminonaphthyl group, N,N-dimethylaminonaphthyl group, N,N-diethylaminonaphthyl group, N,N-dipropylaminonaphthyl group, N,N-dibutylaminonaphthyl group, acetylnaphthyl group, propionylnaphthyl group, butyrylnaphthyl group, methoxycarbonylnaphthyl group, ethoxycarbonylnaphthyl group, propyloxycarbonylnaphthyl group, butyloxycarbonylnaphthyl group, fluoronaphthyl group, chloronaphthyl group, bromonaphthyl group, trifluoromethylnaphthyl group, hydroxynaphthyl group, aminonaphthyl group, biphenyl group, methylbiphenyl group, ethylbiphenyl group, propylbiphenyl group, butylbiphenyl group, methoxybiphenyl group, ethoxybiphenyl group, propyloxybiphenyl group, butyloxybiphenyl group, N-methylaminobiphenyl group, N-ethylaminobiphenyl group, N-propylaminobiphenyl group, N-butylaminobiphenyl group, N,N-dimethylaminobiphenyl group, N,N-diethylaminobiphenyl group, N,N-dipropylaminobiphenyl group, N,N-dibutylaminobiphenyl group, acetylbiphenyl group, propionylbiphenyl group, butyrylbiphenyl group, methoxycarbonylbiphenyl group, ethoxycarbonylbiphenyl group, propyloxycarbonylbiphenyl group, butyloxycarbonylbiphenyl group, fluorobiphenyl group, chlorobiphenyl group, bromobiphenyl group, trifluoromethylbiphenyl group, hydroxybiphenyl group, and aminophenyl group. Among them, those preferably usable can be preferably exemplified, for example, by methylphenyl group, ethylphenyl group, methoxyphenyl group, ethoxyphenyl group, fluorophenyl group, trifluoromethylphenyl group, naphthyl group, and biphenyl group.

The number of the substituent or substituents of the aromatic group described above can be preferably exemplified by 0 to 3, and the number is more preferably 0 or 1. One or two or more of the substituent or substituents as described above can exist independently on the aromatic ring.

$R_5$ described above represents a hydrogen atom, a linear chain or branched chain alkyl group having a number of carbon atom or atoms of 1 to 4, or an acyl group having a linear or branched alkyl chain having a number of carbon atom or atoms of 1 to 4. Specified examples can be preferably exemplified, for example, by a methyl group, an ethyl group, an n-propyl group, an isopropyl group, an n-butyl group, an isobutyl group, a tert-butyl group, an acetyl group, a propionyl group, and a butyryl group. More preferably, it is possible to preferably exemplify a hydrogen atom, a methyl group, and an acetyl group.

$R_6$ described above represents a hydrogen atom or a linear chain or branched chain alkyl group having a number of carbon atom or atoms of 1 to 4. Specified examples can be preferably exemplified, for example, by a hydrogen atom, a methyl group, an ethyl group, an n-propyl group, an isopropyl group, an n-butyl group, an isobutyl group, and a tert-butyl group. More preferably, it is possible to preferably exemplify a hydrogen atom, a methyl group, and an ethyl group.

The compound defined in <2> described above, the isomer thereof, and/or the pharmacologically acceptable salt thereof will be described. In the formula, $R_1$ represents the unsubstituted aromatic group or the aromatic group having the substituent which is an alkyl group having a number of carbon atom or atoms of 1 to 6, more preferably having a number of carbon atom or atoms of 1 to 3, an alkoxy group having an alkyl chain having a number of carbon atom or atoms of 1 to 6, more preferably having a number of carbon atom or atoms of 1 to 3, an alkylamino group having an alkyl chain or chains having a number of carbon atom or atoms of 1 to 6, more preferably having a number of carbon atom or atoms of 1 to 3, an acyl group having an alkyl chain having a number of carbon atom or atoms of 1 to 6, more preferably having a number of carbon atom or atoms of 1 to 3, an ester group having an alkyl chain having a number of carbon atom or atoms of 1 to 6, more preferably having a number of carbon atom or atoms of 1 to 3, a halogen atom, a halogenated alkyl group (preferably a halogenated alkyl group having a number of carbon atom or atoms of 1 to 4), a hydroxy group, or an amino group. Specified examples are exemplified in relation to the unsubstituted aromatic group or the aromatic group having the substituent. It is possible to preferably exemplify, for example, phenyl group, methylphenyl group, ethylphenyl group, propylphenyl group, butylphenyl group, methoxyphenyl group, ethoxyphenyl group, propyloxyphenyl group, butyloxyphenyl group, N-methylaminophenyl group, N-ethylaminophenyl group, N-propylaminophenyl group, N-butylaminophenyl group, N,N,-dimethylaminophenyl group, N,N-diethylaminophenyl group, N,N-dipropylaminophenyl group, N,N-dibutylaminophenyl group, acetylphenyl group, propionylphenyl group, butyrylphenyl group, methoxycarbonylphenyl group, ethoxycarbonylphenyl group, propyloxycarbonylphenyl group, butyloxycarbonylphenyl group, fluorophenyl group, chlorophenyl group, bromophenyl group, trifluoromethylphenyl group, hydroxyphenyl group, aminophenyl group, pyridyl group, methylpyridyl group, ethylpyridyl group, propylpyridyl group, butylpyridyl group, methoxypyridyl group, ethoxypyridyl group, propyloxypyridyl group, butyloxypyridyl group, N-methylaminopyridyl group, N-ethyaminopyridyl group, N-propylaminopyridyl group, N-butylaminopyridyl group, N,N-dimethylaminopyridyl group, N,N-diethylaminopyridyl group, N,N-dipropylaminopyridyl group, N,N-dibutylaminopyridyl group, acetylpyridyl group, propionylpyridyl group, butyrylpyridyl group, methoxycarbonypyridyl group, ethoxycarbonylpyridyl group, propyloxycarbonylpyridyl group, butyloxycarbonylpyridyl group, fluoropyridyl group, chloropyridyl group, bromopyridyl group, trifluoromethylpyridyl group, hydroxypyridyl group, aminopyridyl group, naphthyl group, methylnaphthyl group, ethylnaphthyl group, propylnaphthyl group, butylnaphthyl group, methoxynaphthyl group, ethoxynaphthyl group, propyloxynaphthyl group, butyloxynaphthyl group, N-methylaminonaphthyl group, N-ethylaminonaphthyl group, N-propylaminonaphthyl group, N-butylaminonaphthyl group, N,N-dimethylaminonaphthyl group, N,N-diethylaminonaphthyl group, N,N-dipropylaminonaphthyl group, N,N-dibutylaminonaphthyl group, acetylnaphthyl group, propionylnaphthyl group, butyrylnaphthyl group, methoxycarbonylnaphthyl group, ethoxycarbonylnaphthyl group, propyloxycarbonylnaphthyl group, butyloxycarbonylnaphthyl group, fluoronaphthyl group, chloronaphthyl group, bromonaphthyl group, trifluoromethylnaphthyl group, hydroxynaphthyl group, aminonaphthyl group, biphenyl group, methylbiphenyl group, ethylbiphenyl group, propylbiphenyl group, butylbiphenyl group, methoxybiphenyl group, ethoxybiphenyl group, propyloxybiphenyl group, butyloxybiphenyl group, N-methylaminobiphenyl group, N-ethylaminobiphenyl group, N-propylaminobiphenyl group, N-butylaminobiphenyl group, N,N-dimethylaminobiphenyl group, N,N-diethylaminobiphenyl group, N,N-dipropylaminobiphenyl group, N,N-dibutylaminobiphenyl group, acetylbiphenyl group, propionylbiphenyl group, butyrylbiphenyl group, methoxycarbonylbiphenyl group, ethoxycarbonylbiphenyl group, propyloxycarbonylbiphenyl group, butyloxycarbonylbiphenyl group, fluorobiphenyl group, chlorobiphenyl group, bromobiphenyl group, trifluoromethylbiphenyl group, hydroxybiphenyl group, and aminobiphenyl group. Among them, those preferably usable can be preferably exemplified, for example, by phenyl group, methylphenyl group, ethylphenyl group, methoxyphenyl group, ethoxyphenyl group, fluorophenyl group, trifluoromethylphenyl group, naphthyl group, and biphenyl group.

The number of the substituent or substituents of the aromatic group described above can be preferably exemplified by 0 to 3, and the number is more preferably 0 or 1. One or two or more of the substituent or substituents as described above can exist independently on the aromatic ring.

$R_2$ described above represents a hydrogen atom, a methyl group, an ethyl group, an n-propyl group, an isopropyl group, an n-butyl group, an isobutyl group, a tert-butyl group, an acetyl group, a propionyl group, or a butyryl group. Specified examples can be preferably exemplified by a hydrogen atom, a methyl group, and an acetyl group.

$R_3$ described above represents a hydrogen atom, a methyl group, an ethyl group, an n-propyl group, an isopropyl group, an n-butyl group, an isobutyl group, or a tert-butyl group. Specified examples can be preferably exemplified by a hydrogen atom, a methyl group, and an ethyl group.

The compound defined in <2> described above, the isomer thereof, and/or the pharmacologically acceptable salt thereof as well as the compound defined in <6> described above, the isomer thereof, and/or the pharmacologically acceptable salt thereof has/have the excellent function to prevent or ameliorate (improve) the pigmentation. Further, the compounds are excellent in the solubility in the hydrophilic or lipophilic medium, and it is easy to produce or formulate the pharmaceutical preparation such as the external preparation for skin or the like. Further, the compounds are excellent in the stability in the pharmaceutical preparation and the skin retention, and the compounds exhibit the excellent effect to prevent or ameliorate (improve) the pigmentation.

The compound defined in <6> described above, the isomer thereof, and/or the pharmacologically acceptable salt thereof will be described. In the formula, $R_4$ represents the unsubstituted aromatic group or the aromatic group having the substituent which is an alkyl group having a number of carbon atom or atoms of 1 to 6, more preferably having a number of carbon atom or atoms of 1 to 3, an alkoxy group having an alkyl chain having a number of carbon atom or atoms of 1 to 6, more preferably having a number of carbon atom or atoms of 1 to 3, an alkylamino group having an alkyl chain or chains having a number of carbon atom or atoms of 1 to 6, more preferably having a number of carbon atom or atoms of 1 to 3, an acyl group having an alkyl chain having a number of carbon atom or atoms of 1 to 6, more preferably having a number of carbon atom or atoms of 1 to 3, an ester group having an alkyl chain having a number of carbon atom or atoms of 1 to 6, more preferably having a number of carbon atom or atoms of 1 to 3, a halogen atom, a halogenated alkyl group (preferably a halogenated alkyl group having a number of carbon atom or atoms of 1 to 4), a hydroxy group, or an amino group (provided that unsubstituted phenyl group is excluded).

Specified examples are exemplified in relation to the unsubstituted aromatic group or the aromatic group having the substituent. It is possible to preferably exemplify, for example, methylphenyl group, ethylphenyl group, propylphenyl group, butylphenyl group, methoxyphenyl group, ethoxyphenyl group, propyloxyphenyl group, butyloxyphenyl group, N-methylaminophenyl group, N-ethylaminophenyl group, N-propylaminophenyl group, N-butylaminophenyl group, N,N,-dimethylaminophenyl group, N,N-diethylaminophenyl group, N,N-dipropylaminophenyl group, N,N-dibutylaminophenyl group, acetylphenyl group, propionylphenyl group, butyrylphenyl group, methoxycarbonylphenyl group, ethoxycarbonylphenyl group, propyloxycarbonylphenyl group, butyloxycarbonylphenyl group, fluorophenyl group, chlorophenyl group, bromophenyl group, trifluoromethylphenyl group, hydroxyphenyl group, aminophenyl group, pyridyl group, methylpyridyl group, ethylpyridyl group, propylpyridyl group, butylpyridyl group, methoxypyridyl group, ethoxypyridyl group, propyloxypyridyl group, butyloxypyridyl group, N-methylaminopyridyl group, N-ethyaminopyridyl group, N-propylaminopyridyl group, N-butylaminopyridyl group, N,N-dimethylaminopyridyl group, N,N-diethylaminopyridyl group, N,N-dipropylaminopyridyl group, N,N-dibutylaminopyridyl group, acetylpyridyl group, propionylpyridyl group, butyrylpyridyl group, methoxycarbonypyridyl group, ethoxycarbonylpyridyl group, propyloxycarbonylpyridyl group, butyloxycarbonylpyridyl group, fluoropyridyl group, chloropyridyl group, bromopyridyl group, trifluoromethylpyridyl group, hydroxypyridyl group, aminopyridyl group, naphthyl group, methylnaphthyl group, ethylnaphthyl group, propylnaphthyl group, butylnaphthyl group, methoxynaphthyl group, ethoxynaphthyl group, propyloxynaphthyl group, butyloxynaphthyl group, N-methylaminonaphthyl group, N-ethylaminonaphthyl group, N-propylaminonaphthyl group, N-butylaminonaphthyl group, N,N-dimethylaminonaphthyl group, N,N-diethylaminonaphthyl group, N,N-dipropylaminonaphthyl group, N,N-dibutylaminonaphthyl group, acetylnaphthyl group, propionylnaphthyl group, butyrylnaphthyl group, methoxycarbonylnaphthyl group, ethoxycarbonylnaphthyl group, propyloxycarbonylnaphthyl group, butyloxycarbonylnaphthyl group, fluoronaphthyl group, chloronaphthyl group, bromonaphthyl group, trifluoromethylnaphthyl group, hydroxynaphthyl group, aminonaphthyl group, biphenyl group, methylbiphenyl group, ethylbiphenyl group, propylbiphenyl group, butylbiphenyl group, methoxybiphenyl group, ethoxybiphenyl group, propyloxybiphenyl group, butyloxybiphenyl group, N-methylaminobiphenyl group, N-ethylaminobiphenyl group, N-propylaminobiphenyl group, N-butylaminobiphenyl group, N,N-dimethylaminobiphenyl group, N,N-diethylaminobiphenyl group, N,N-dipropylaminobiphenyl group, N,N-dibutylaminobiphenyl group, acetylbiphenyl group, propionylbiphenyl group, butyrylbiphenyl group, methoxycarbonylbiphenyl group, ethoxycarbonylbiphenyl group, propyloxycarbonylbiphenyl group, butyloxycarbonylbiphenyl group, fluorobiphenyl group, chlorobiphenyl group, bromobiphenyl group, trifluoromethylbiphenyl group, hydroxybiphenyl group, and aminobiphenyl group. Among them, those preferably usable can be preferably exemplified, for example, by methylphenyl group, ethylphenyl group, methoxyphenyl group, ethoxyphenyl group, fluorophenyl group, trifluoromethylphenyl group, naphthyl group, and biphenyl group.

The number of the substituent or substituents of the aromatic group described above can be preferably exemplified by 0 to 3, and the number is more preferably 0 or 1. One or two or more of the substituent or substituents as described above can exist independently on the aromatic ring.

$R_5$ described above represents a hydrogen atom, a methyl group, an ethyl group, an n-propyl group, an isopropyl group, an n-butyl group, an isobutyl group, a tert-butyl group, an acetyl group, a propionyl group, or a butyryl group. Specified examples can be preferably exemplified by a hydrogen atom, a methyl group, and an acetyl group.

$R_6$ described above represents a hydrogen atom, a methyl group, an ethyl group, an n-propyl group, an isopropyl group, an n-butyl group, an isobutyl group, or a tert-butyl group. Specified examples can be preferably exemplified by a hydrogen atom, a methyl group, and an ethyl group.

However, at least one of $R_5$ and $R_6$ is any group other than the hydrogen atom when $R_4$ is the phenyl group having the substituent or the unsubstituted naphthyl group.

The compound defined in <3> described above, the isomer thereof, and/or the pharmacologically acceptable salt thereof will be described. In the formula, $R_1$ represents an unsubstituted phenyl, naphthyl, or biphenyl group or a phenyl, naphthyl, or biphenyl group having the substituent which is an alkyl group having a number of carbon atom or atoms of 1 to 6, more preferably having a number of carbon atom or atoms of 1 to 3, an alkoxy group having an alkyl chain having a number of carbon atom or atoms of 1 to 6, more preferably having a number of carbon atom or atoms of 1 to 3, an alkylamino group having an alkyl chain or chains having a number of carbon atom or atoms of 1 to 6, more preferably having a number of carbon atom or atoms of 1 to 3, an acyl group having an alkyl chain having a number of carbon atom or atoms of 1 to 6, more preferably having a number of carbon atom or atoms of 1 to 3, an ester group having an alkyl chain having a number of carbon atom or atoms of 1 to 6, more preferably having a number of carbon atom or atoms of 1 to 3, a halogen atom, a halogenated alkyl group (preferably a halogenated alkyl group having a number of carbon atom or atoms of 1 to 4), a hydroxy group, or an amino group.

Specified examples are exemplified in relation to the unsubstituted phenyl, naphthyl, or biphenyl group or the phenyl, naphthyl, or biphenyl group having the substituent. It is possible to preferably exemplify, for example, phenyl group, methylphenyl group, ethylphenyl group, propylphenyl group, butylphenyl group, methoxyphenyl group, ethoxyphenyl group, propyloxyphenyl group, butyloxyphenyl group, N-methylaminophenyl group, N-ethylaminophenyl group, N-propylaminophenyl group, N-butylaminophenyl group, N,N,-dimethylaminophenyl group, N,N-diethylaminophenyl group, N,N-dipropylaminophenyl group, N,N-dibutylaminophenyl group, acetylphenyl group, propionylphenyl group, butyrylphenyl group, methoxycarbonylphenyl group, ethoxycarbonylphenyl group, propyloxycarbonylphenyl group, butyloxycarbonylphenyl group, fluorophenyl group, chlorophenyl group, bromophenyl group, trifluoromethylphenyl group, hydroxyphenyl group, aminophenyl group, naphthyl group, methylnaphthyl group, ethylnaphthyl group, propylnaphthyl group, butylnaphthyl group, methoxynaphthyl group, ethoxynaphthyl group, propyloxynaphthyl group, butyloxynaphthyl group, N-methylaminonaphthyl group, N-ethylaminonaphthyl group, N-propylaminonaphthyl group, N-butylaminonaphthyl group, N,N-dimethylaminonaphthyl group, N,N-diethylaminonaphthyl group, N,N-dipropylaminonaphthyl group, N,N-dibutylaminonaphthyl group, acetylnaphthyl group, propionylnaphthyl group, butyrylnaphthyl group, methoxycarbonylnaphthyl group, ethoxycarbonylnaphthyl group, propyloxycarbonylnaphthyl group, butyloxycarbonylnaphthyl group, fluoronaphthyl group, chloronaphthyl group, bromonaphthyl group, trifluoromethylnaphthyl group, hydroxynaphthyl group, aminonaphthyl group, biphenyl group, methylbiphenyl group, ethylbiphenyl group, propylbiphenyl group, butylbiphenyl group, methoxybiphenyl group, ethoxybiphenyl group, propyloxybiphenyl group, butyloxybiphenyl group, N-methylaminobiphenyl group, N-ethylaminobiphenyl group, N-propylaminobiphenyl group, N-butylaminobiphenyl group, N,N-dimethylaminobiphenyl group, N,N-diethylaminobiphenyl group, N,N-dipropylaminobiphenyl group, N,N-dibutylaminobiphenyl group, acetylbiphenyl group, propionylbiphenyl group, butyrylbiphenyl group, methoxycarbonylbiphenyl group, ethoxycarbonylbiphenyl group, propyloxycarbonylbiphenyl group, butyloxycarbonylbiphenyl group, fluorobiphenyl group, chlorobiphenyl group, bromobiphenyl group, trifluoromethylbiphenyl group, hydroxybiphenyl group, and aminobiphenyl group. Among them, those preferably usable can be preferably exemplified, for example, by phenyl group, methylphenyl group, ethylphenyl group, methoxyphenyl group, ethoxyphenyl group, fluorophenyl group, trifluoromethylphenyl group, naphthyl group, and biphenyl group.

The number of the substituent or substituents on the phenyl, naphthyl, or biphenyl group described above can be preferably exemplified by 0 to 3, and the number is more preferably 0 or 1. One or two or more of the substituent or substituents as described above can exist independently on the phenyl, naphthyl, or biphenyl group.

$R_2$ described above represents a hydrogen atom, a methyl group, or an acetyl group.

$R_3$ described above represents a hydrogen atom, a methyl group, or an ethyl group.

The compound defined in <3> described above, the isomer thereof, and/or the pharmacologically acceptable salt thereof as well as the compound defined in <7> described above, the isomer thereof, and/or the pharmacologically acceptable salt thereof has/have the excellent function to prevent or ameliorate (improve) the pigmentation. Further, the compounds are excellent in the solubility in the hydrophilic or lipophilic medium, and it is easy to produce or formulate the pharmaceutical preparation such as the external preparation for skin or the like. Further, the compounds are excellent in the stability in the pharmaceutical preparation and the skin retention, and the compounds exhibit the excellent effect to prevent or ameliorate (improve) the pigmentation.

The compound defined in <7> described above, the isomer thereof, and/or the pharmacologically acceptable salt thereof will be described. In the formula, $R_4$ represents an unsubstituted phenyl, naphthyl, or biphenyl group or a phenyl, naphthyl, or biphenyl group having the substituent which is an alkyl group having a number of carbon atom or atoms of 1 to 6, more preferably having a number of carbon atom or atoms of 1 to 3, an alkoxy group having an alkyl chain having a number of carbon atom or atoms of 1 to 6, more preferably having a number of carbon atom or atoms of 1 to 3, an alkylamino group having an alkyl chain or chains having a number of carbon atom or atoms of 1 to 6, more preferably having a number of carbon atom or atoms of 1 to 3, an acyl group having an alkyl chain having a number of carbon atom or atoms of 1 to 6, more preferably having a number of carbon atom or atoms of 1 to 3, an ester group having an alkyl chain having a number of carbon atom or atoms of 1 to 6, more preferably having a number of carbon atom or atoms of 1 to 3, a halogen atom, a halogenated alkyl group (preferably a halogenated alkyl group having a number of carbon atom or atoms of 1 to 4), a hydroxy group, or an amino group (provided that unsubstituted phenyl group is excluded).

Specified examples are exemplified in relation to the unsubstituted phenyl, naphthyl, or biphenyl group or the phenyl, naphthyl, or biphenyl group having the substituent. It is possible to preferably exemplify, for example, methylphenyl group, ethylphenyl group, propylphenyl group, butylphenyl group, methoxyphenyl group, ethoxyphenyl group, propyloxyphenyl group, butyloxyphenyl group, N-methylaminophenyl group, N-ethylaminophenyl group, N-propylaminophenyl group, N-butylaminophenyl group, N,N,-dimethylaminophenyl group, N,N-diethylaminophenyl group, N,N-dipropylaminophenyl group, N,N-dibutylaminophenyl group, acetylphenyl group, propionylphenyl group, butyrylphenyl group, methoxycarbonylphenyl group, ethoxycarbonylphenyl group, propyloxycarbonylphenyl group, butyloxycarbonylphenyl group, fluorophenyl group, chlorophenyl group, bromophenyl group, trifluoromethylphenyl group, hydroxyphenyl group, aminophenyl group, naphthyl group, methylnaphthyl group, ethylnaphthyl group, propylnaphthyl group, butylnaphthyl group, methoxynaphthyl group, ethoxynaphthyl group, propyloxynaphthyl group, butyloxynaphthyl group, N-methylaminonaphthyl group, N-ethylaminonaphthyl group, N-propylaminonaphthyl group, N-butylaminonaphthyl group, N,N-dimethylaminonaphthyl group, N,N-diethylaminonaphthyl group, N,N-dipropylaminonaphthyl group, N,N-dibutylaminonaphthyl group, acetylnaphthyl group, propionylnaphthyl group, butyrylnaphthyl group, methoxycarbonylnaphthyl group, ethoxycarbonylnaphthyl group, propyloxycarbonylnaphthyl group, butyloxycarbonylnaphthyl group, fluoronaphthyl group, chloronaphthyl group, bromonaphthyl group, trifluoromethylnaphthyl group, hydroxynaphthyl group, aminonaphthyl group, biphenyl group, methylbiphenyl group, ethylbiphenyl group, propylbiphenyl group, butylbiphenyl group, methoxybiphenyl group, ethoxybiphenyl group, propyloxybiphenyl group, butyloxybiphenyl group, N-methylaminobiphenyl group, N-ethylaminobiphenyl group, N-propylaminobiphenyl group, N-butylaminobiphenyl group, N,N-dimethylaminobiphenyl group, N,N-diethylaminobiphenyl group, N,N-dipropylaminobiphenyl group, N,N-dibutylaminobiphenyl group, acetylbiphenyl group, propionylbiphenyl group, butyrylbiphenyl group, methoxycarbonylbiphenyl group, ethoxycarbonylbiphenyl group, propyloxycarbonylbiphenyl group, butyloxycarbonylbiphenyl group, fluorobiphenyl group, chlorobiphenyl group, bromobiphenyl group, trifluoromethylbiphenyl group, hydroxybiphenyl group, and aminobiphenyl group. Among them, those preferably usable can be preferably exemplified, for example, by methylphenyl group, ethylphenyl group, methoxyphenyl group, ethoxyphenyl group, fluorophenyl group, trifluoromethylphenyl group, naphthyl group, and biphenyl group.

The number of the substituent or substituents on the phenyl, naphthyl, or biphenyl group described above can be preferably exemplified by 0 to 3, and the number is more preferably 0 or 1. One or two or more of the substituent or substituents as described above can exist independently on the phenyl, naphthyl, or biphenyl group.

$R_5$ described above represents a hydrogen atom, a methyl group, or an acetyl group.

$R_6$ described above represents a hydrogen atom, a methyl group, or an ethyl group.

However, at least one of $R_5$ and $R_6$ is any group other than the hydrogen atom when $R_4$ is the phenyl group having the substituent or the unsubstituted naphthyl group.

Specified examples are exemplified in relation to the compound represented by the general formula (1) or the compound represented by the general formula (2) described above. It is possible to preferably exemplify 3-hydroxy-2-(benzoylamino)propionic acid (Compound 2), 3-hydroxy-2-(methylbenzoylamino)propionic acid (Compounds 1, 3, 15), 3-acetoxy-2-(methylbenzoylamino)propionic acid (Compound 11), 3-acetoxy-2-(ethylbenzoyl)propionic acid, 3-acetoxy-2-(methylbenzoyl)propionic acid, 3-acetoxy-2-(methylnaphthyl)propionic acid, 3-acetoxy-2-(methoxynaphthyl)propionic acid, 2-(methylbenzoyl)-3-propionyloxypropionic acid, 2-(ethylbenzoylamino)-3-hydroxypropionic acid (Compound 7), 3-hydroxy-2-(propylbenzoylamino)propionic acid, 2-(butylbenzoylamino)-3-hydroxypropionic acid, 3-hydroxy-2-(methoxybenzoylamino)propionic acid (Compound 5), 2-(ethoxybenzoylamino)-3-hydroxypropionic acid, 3-hydroxy-2-(propyloxybenzoylamino)propionic acid, 2-(butyloxybenzoylamino)-3-hydroxypropionic acid, 3-hydroxy-2-(N-methylbenzoylamino)propionic acid, 2-(N-ethylbenzoylamino)-3-hydroxypropionic acid, 3-hydroxy-2-(N-propylbenzoylamino)propionic acid, 2-(N,N-dimethylbenzoylamino)-3-hydroxypropionic acid, 2-(N,N-diethylbenzoylamino)-3-hydroxypropionic acid, 2-(N,N-dipropylbenzoylamino)-3-hydroxypropionic acid, 2-(acetylbenzoylamino)-3-hydroxypropionic acid, 3-hydroxy-2-(valerylbenzoylamino)propionic acid, 3-hydroxy-2-(propionylbenzoylamino)propionic acid, 3-hydroxy-2-(methoxycarbonylbenzoylamino)propionic acid, 2-(ethoxycarbonylbenzoylamino)-3-hydroxypropionic acid, 3-hydroxy-2-(propyloxycarbonylbenzoylamino)propionic acid, 2-(chlorobenzoylamino)-3-hydroxypropionic acid, 2-(fluorobenzoylamino)-3-hydroxypropionic acid (Compound 4), 3-hydroxy-2-(trifluoromethylbenzoylamino)propionic acid (Compound 8), 3-hydroxy-2-(hydroxybenzoylamino)propionic acid, 2-(aminobenzoylamino)-3-hydroxypropionic acid, 3-hydroxy-2-(biphenylamino)propionic acid (Compound 14), 3-hydroxy-2-(methylbiphenylamino)propionic acid, 2-(ethylbiphenylamino)-2-hydroxypropionic acid, 3-hydroxy-2-(methoxybiphenylamino)propionic acid, 2-(ethoxybiphenylamino)-3-hydroxypropionic acid;

3-hydroxy-2-(pyridinecarbonylamino)propionic acid, 3-hydroxy-2-(methylpyridinecarbonylamino)propionic acid, 2-(ethylpyridinecarbonylamino)-3-hydroxypropionic acid, 3-hydroxy-2-(propylpyridinecarbonylamino)propionic acid, 2-(butylpyridinecarbonylamino)-3-hydroxypropionic acid, 3-hydroxy-2-(methoxypyridinecarbonylamino)propionic acid, 2-(ethoxypyridinecarbonylamino)-3-hydroxypropionic acid, 3-hydroxy-2-(propyloxypyridinecarbonylamino)propionic acid, 2-(butyloxypyridinecarbonylamino)-3-hydroxypropionic acid, 3-hydroxy-2-(N-methylaminopyridinecarbonylamino)propionic acid, 2-(N-ethylaminopyridinecarbonylamino)-3-hydroxypropionic acid, 2-(N,N-dimethylaminopyridinecarbonylamino)-3-hydroxypropionic acid, 2-(N,N-diethylaminopyridinecarbonylamino)-3-hydroxypropionic acid, 2-(acetylpyridinecarbonylamino)-3-hydroxypropionic acid, 3-hydroxy-2-(valerylpyridinecarbonylamino)propionic acid, 2-(chloropyridinecarbonylamino)-3-hydroxypropionic acid, 2-(fluoropyridinecarbonylamino)-3-hydroxypropionic acid, 3-hydroxy-2-(trifluoromethylpyridinecarbonylamino)propionic acid, 3-hydroxy-2-(hydroxypyridinecarbonylamino)propionic acid, 2-(aminopyridinecarbonylamino)-3-hydroxypropionic acid, 3-hydroxy-2-(naphthoylamino)propionic acid (Compound 10), 3-hydroxy-2-(methylnaphthoylamino)propionic acid, 2-(ethylnaphthoylamino)-3-hydroxypropionic acid, 3-hydroxy-2-(propylnaphthoylamino)propionic acid, 3-hydroxy-2-(methoxynaphthoylamino)propionic acid, 2-(ethoxynaphthoylamino)-3-hydroxypropionic acid, 3-hydroxy-2-(N-methylnaphthoylamino)propionic acid, 2-(N-ethylnaphthoylamino)-3-hydroxypropionic acid, 2-(N,N-dimethylaminonaphthoylamino)-3-hydroxypropionic acid, 2-(N,N-diethylaminonaphthoylamino)-3-hydroxypropionic acid, 2-(acetylnaphthoylamino)-3-hydroxypropionic acid, 3-hydroxy-2-(valerylnaphthoylamino)propionic acid, 3-hydroxy-2-(methoxycarbonylnaphthoylamino)propionic acid, 2-(ethoxycarbonylnaphthoylamino)-3-hydroxypropionic acid, 2-(chloronaphthoylamino)-3-hydroxypropionic acid, 2-(fluoronaphthoylamino)-3-hydroxypropionic acid, 3-hydroxy-2-(trifluoromethylnaphthoylamino)propionic acid, 3-hydroxy-2-(hydroxynaphthoylamino)propionic acid, 2-(aminonaphthoylamino)-3-hydroxypropionic acid, 3-hydroxy-2-(biphenylcarbonylamino)propionic acid, 3-hydroxy-2-(methylbiphenylcarbonylamino)propionic acid, 2-(ethylbiphenylcarbonylamino)-3-hydroxypropionic acid, 3-hydroxy-2-(propylbiphenylcarbonylamino)propionic acid, 3-hydroxy-2-(methoxybiphenylcarbonylamino)propionic acid, 2-(ethoxybiphenylcarbonylamino)-3-hydroxypropionic acid, 3 hydroxy-2-(N-methylaminobiphenylcarbonylamino)propionic acid, 2-(N-ethylaminobiphenylcarbonylamino)propionic acid, 2-(N,N-dimethylaminobiphenylcarbonylamino)-3-hydroxypropionic acid, 2-(N,N-diethylaminobiphenylcarbonylamino)-3-hydroxypropionic acid, 2-(acetylbiphenylcarbonylamino)-3-hydroxypropionic acid, 3-hydroxy-2-(2-valerylbiphenylcarbonylamino)propionic acid, 3-hydroxy-2-(methoxycarbonylbiphenylcarbonylamino)propionic acid, 2-(ethoxycarbonylbiphenylcarbonylamino)-3-hydroxypropionic acid, 2-(chlorobiphenylcarbonylamino)-3-hydroxypropionic acid, 2-(fluorobiphenylcarbonylamino)-3-hydroxypropionic acid, 3-hydroxy-2-(trifluoromethylbiphenylcarbonylamino)propionic acid, 3-hydroxy-2-(hydroxybiphenylcarbonylamino)propionic acid, 2-(aminobiphenylcarbonylamino)-3-hydroxypropionic acid;

3-methoxy-2-(benzoylamino)propionic acid (Compound 16), 3-methoxy-2-(methylbenzoylamino)propionic acid (Compound 9), 2-(ethylbenzoylamino)-3-methoxypropionic acid, 3-methoxy-2-(propylbenzoylamino)propionic acid, 3-methoxy-2-(methoxybenzoylamino)propionic acid, (ethoxybenzoylamino)-3-methoxypropionic acid, 2-(chlorobenzoylamino)-3-methoxypropionic acid, 2-(fluorobenzoylamino)-3-methoxypropionic acid, 3-methoxy-2-(trifluoromethylbenzoylamino)propionic acid, 3-ethoxy-2-(methylbenzoylamino)propionic acid, 3-ethoxy-2-(ethylbenzoylamino)propionic acid, 3-ethoxy-2-(propylbenzoylamino)propionic acid, 3-ethoxy-2-(methoxybenzoylamino)propionic acid, 3-ethoxy-2-(ethoxybenzoylamino)propionic acid, 3-ethoxy-2-(chlorobenzoylamino)propionic acid, 3-ethoxy-2-(fluorobenzoylamino)propionic acid, 3-ethoxy-2-(trifluoromethylbenzoylamino)propionic acid, 3-hydroxy-2-(methylbenzoylamino)propionic acid methyl ester (Compound 6), 2-(ethylbenzoylamino)-3-hydroxypropionic acid methyl ester, 3-hydroxy-2-(propylbenzoylamino)propionic acid methyl ester, 3-hydroxy-2-(methoxybenzoylamino)propionic acid methyl ester, 2-(chlorobenzoylamino)-3-hydroxypropionic acid methyl ester, 2-(fluorobenzoylamino)propionic acid methyl ester, 3-hydroxy-2-(trifluoromethylbenzoylamino)propionic acid methyl ester, 3-hydroxy-2-(methylbenzoylamino)propionic acid ethyl ester (Compound 17), 2-(ethylbenzoylamino)-3-hydroxypropionic acid ethyl ester, 3-hydroxy-2-(propylbenzoylamino)propionic acid ethyl ester, 3-hydroxy-2-(methoxybenzoylamino)propionic acid ethyl ester, 2-(chlorobenzoylamino)-3-hydroxypropionic acid ethyl ester, 2-(fluorobenzoylamino)-3-hydroxypropionic acid ethyl ester, 3-hydroxy-2-(trifluoromethylbenzoylamino)propionic acid ethyl ester, 3-methoxy-2-(methylbenzoylamino)propionic acid methyl ester, 3-methoxy-2-(ethylbenzoylamino)propionic acid methyl ester, 3-methoxy-2-(propylbenzoylamino)propionic acid methyl ester, 3-methoxy-2-(methoxybenzoylamino)propionic acid methyl ester, 2-(chlorobenzoylamino)-3-methoxypropionic acid methyl ester, 2-(fluorobenzoylamino)-3-methoxypropionic acid methyl ester, 3-methoxy-2-(trifluoromethylbenzoylamino)propionic acid methyl ester, 3-ethoxy-2-(methylbenzoylamino)propionic acid ethyl ester, 3-ethoxy-2-(ethylbenzoylamino)propionic acid ethyl ester, 3-ethoxy-2-(propylbenzoylamino)propionic acid ethyl ester, 3-ethoxy-2-(methoxybenzoylamino)propionic acid ethyl ester, 2-(chlorobenzoylamino)-3-ethoxypropionic acid ethyl ester, 3-ethoxy-2-(fluorobenzoylamino)propionic acid ethyl ester, 3-ethoxy-2-(trifluoromethylbenzoylamino)propionic acid ethyl ester, 3-methoxy-2-(pyridinecarbonylamino)propionic acid, 3-methoxy-2-(methylpyridinecarbonylamino)propionic acid, 2-(ethylpyridinecarbonylamino)-3-methoxypropionic acid, 3-methoxy-2-(methoxypyridinecarbonylamino)propionic acid, 2-(ethoxypyridinecarbonylamino)-3-methoxypropionic acid, 2-(chloropyridinecarbonylamino)-3-methoxypropionic acid, 2-(fluoropyridinecarbonylamino)-3-methoxypropionic acid, 3-methoxy-2-(trifluoromethylpyridinecarbonylamino)propionic acid, 2-(hydroxypyridinecarbonylamino)-3-methoxypropionic acid, 2-(aminopyridinecarbonylamino)-3-methoxypropionic acid, 3-ethoxy-2-(pyridinecarbonylamino)propionic acid, 3-ethoxy-2-(methylpyridinecarbonylamino)propionic acid, 3-ethoxy-2-(ethylpyridinecarbonylamino)propionic acid, 3-ethoxy-2-(methoxypyridinecarbonylamino)propionic acid, 3-ethoxy-2-(ethoxypyridinecarbonylamino)propionic acid, 2-(chloropyridinecarbonylamino)-3-ethoxypropionic acid, 3-ethoxy-2-(fluoropyridinecarbonylamino)propionic acid, 3-ethoxy-2-(trifluoromethylpyridinecarbonylamino) propionic acid, 3-ethoxy-2-(hydroxypyridinecarbonylamino) propionic acid, 2-(aminopyridinecarbonylamino)-3-ethoxypropionic acid, 3-hydroxy-2-(pyridinecarbonylamino)propionic acid methyl ester, 3-hydroxy-2-(methylpyridinecarbonylamino)propionic acid methyl ester, 2-(ethylpyridinecarbonylamino)-3-hydroxypropionic acid methyl ester, 3-hydroxy-2-(methoxypyridinecarbonylamino)propionic acid methyl ester, 2-(ethoxypyridinecarbonylamino)-3-hydroxypropionic acid methyl ester, 2-(chloropyridinecarbonylamino)-3-hydroxypropionic acid methyl ester, 2-(fluoropyridinecarbonylamino)propionic acid methyl ester, 3-hydroxy-2-(trifluoromethylpyridinecarbonylamino)propionic acid methyl ester, 3-hydroxy-2-(hydroxypyridinecarbonylamino)propionic acid methyl ester, 2-(aminopyridinecarbonylamino)-3-hydroxypropionic acid methyl ester, 3-hydroxy-2-(pyridinecarbonylamino)propionic acid ethyl ester, 3-hydroxy-2-(methylpyridinecarbonylamino)propionic acid ethyl ester, 2-(ethylpyridinecarbonylamino)-3-hydroxypropionic acid ethyl ester, 3-hydroxy-2-(methoxypyridinecarbonylamino)propionic acid ethyl ester, 2-(ethoxypyridinecarbonylamino)-3-hydroxypropionic acid ethyl ester, 2-(chloropyridinecarbonylamino)-3-hydroxypropionic acid ethyl ester, 2-(fluoropyridinecarbonylamino)propionic acid ethyl ester, 3-hydroxy-2-(trifluoromethylpyridinecarbonylamino)propionic acid ethyl ester, 3-hydroxy-2-

(hydroxypyridinecarbonylamino)propionic acid ethyl ester, 2-(aminopyridinecarbonylamino)-3-hydroxypropionic acid ethyl ester, 3-methoxy-2-(pyridinecarbonylamino)propionic acid methyl ester, 3-methoxy-2-(methylpyridinecarbonylamino)propionic acid methyl ester, 2-(ethylpyridinecarbonylamino)-3-methoxypropionic acid methyl ester, 3-methoxy-2-(methoxypyridinecarbonylamino)propionic acid methyl ester, 2-(ethoxypyridinecarbonylamino)-3-methoxypropionic acid methyl ester, 2-(chloropyridinecarbonylamino)-3-methoxypropionic acid methyl ester, 2-(fluoropyridinecarbonylamino)-3-methoxypropionic acid methyl ester, 3-methoxy-2-(trifluoromethylpyridinecarbonylamino)propionic acid methyl ester, 2-(hydroxypyridinecarbonylamino)-3-methoxypropionic acid methyl ester, 2-(aminopyridinecarbonylamino)-3-methoxypropionic acid methyl ester, 3-ethoxy-2-(pyridinecarbonylamino)propionic acid ethyl ester, 3-ethoxy-2-(methylpyridinecarbonylamino)propionic acid ethyl ester, 3-ethoxy-2-(ethylpyridinecarbonylamino)propionic acid ethyl ester, 3-ethoxy-2-(methoxypyridinecarbonylamino)propionic acid ethyl ester, 3-ethoxy-2-(ethoxypyridinecarbonylamino)propionic acid ethyl ester, 2-(chloropyridinecarbonylamino)-3-ethoxypropionic acid ethyl ester, 3-ethoxy-2-(fluoropyridinecarbonylamino)propionic acid ethyl ester, 3-ethoxy-2-(trifluoromethylpyridinecarbonylamino)propionic acid ethyl ester, 3-ethoxy-2-(hydroxypyridinecarbonylamino)propionic acid ethyl ester, 2-(aminopyridinecarbonylamino)-3-ethoxypropionic acid ethyl ester, 3-methoxy-2-(naphthoylamino)propionic acid (Compound 13), 3-methoxy-2-(methylnaphthoylamino)propionic acid, 2-(ethylnaphthoylamino)-3-methoxypropionic acid, 3-methoxy-2-(propylnaphthoylamino)propionic acid, 3-methoxy-2-(methoxynaphthoylamino)propionic acid, 3-methoxy-2-(ethoxynaphthoylamino)propionic acid, 2-(chloronaphthoylamino)-3-methoxypropionic acid, 2-(fluoronaphthoylamino)-3-methoxypropionic acid, 3-methoxy-2-(trifluoromethylnaphthoyl)propionic acid, 3-ethoxy-2-(methylnaphthoylamino)propionic acid, 3-ethoxy-2-(ethylnaphthoylamino)propionic acid, 3-ethoxy-2-(propylnaphthoylamino)propionic acid, 3-ethoxy-2-(methoxynaphthoylamino)propionic acid, 3-ethoxy-2-(ethoxynaphthoylamino)propionic acid, 3-ethoxy-2-(chloronaphthoylamino)propionic acid, 3-ethoxy-2-(fluoronaphthoylamino)propionic acid, 3-ethoxy-2-(trifluoromethylnaphthoyl)propionic acid, 3-hydroxy-2-(naphthoylamino)propionic acid methyl ester (Compound 12), 3-hydroxy-2-(methylnaphthoylamino)propionic acid methyl ester, 2-(ethylnaphthoylamino)-3-hydroxypropionic acid methyl ester, 3-hydroxy-2-(propylnaphthoylamino)propionic acid methyl ester, 3-hydroxy-2-(methoxynaphthoylamino)propionic acid methyl ester, 2-(ethoxynaphthoylamino)-3-hydroxypropionic acid methyl ester, 2-(chloronaphthoylamino)-3-hydroxypropionic acid methyl ester, 2-(fluoronaphthoylamino)-3-hydroxypropionic acid methyl ester, 3-hydroxy-2-(trifluoromethylnaphthoyl)propionic acid methyl ester, 3-hydroxy-2-(naphthoylamino)propionic acid ethyl ester, 3-hydroxy-2-(methylnaphthoylamino)propionic acid ethyl ester, 2-(ethylnaphthoylamino)-3-hydroxypropionic acid ethyl ester, 3-hydroxy-2-(propylnaphthoylamino)propionic acid ethyl ester, 3-hydroxy-2-(methoxynaphthoylamino)propionic acid ethyl ester, 2-(ethoxynaphthoylamino)-3-hydroxypropionic acid ethyl ester, 2-(chloronaphthoylamino)-3-hydroxypropionic acid ethyl ester, 2-(fluoronaphthoylamino)-3-hydroxypropionic acid ethyl ester, 3-hydroxy-2-(trifluoromethylnaphthoyl)propionic acid ethyl ester, 3-methoxy-2-(methylnaphthoylamino)propionic acid methyl ester, 2-(ethylnaphthoylamino)-3-methoxypropionic acid methyl ester, 3-methoxy-2-(propylnaphthoylamino)propionic acid methyl ester, 3-methoxy-2-(methoxynaphthoylamino)propionic acid methyl ester, 3-methoxy-2-(ethoxynaphthoylamino)propionic acid methyl ester, 2-(chloronaphthoylamino)-3-methoxypropionic acid methyl ester, 2-(fluoronaphthoylamino)-3-methoxypropionic acid methyl ester, 3-methoxy-2-(trifluoromethylnaphthoyl)propionic acid methyl ester, 3-ethoxy-2-(methylnaphthoylamino)propionic acid ethyl ester, 3-ethoxy-2-(ethylnaphthoylamino)propionic acid ethyl ester, 3-ethoxy-2-(propylnaphthoylamino)propionic acid ethyl ester, 3-ethoxy-2-(methoxynaphthoylamino)propionic acid ethyl ester, 3-ethoxy-2-(ethoxynaphthoylamino)propionic acid ethyl ester, 3-ethoxy-2-(chloronaphthoylamino)propionic acid ethyl ester, 3-ethoxy-2-(fluoronaphthoylamino)propionic acid ethyl ester, 3-ethoxy-2-(trifluoromethylnaphthoyl)propionic acid ethyl ester, isomers thereof, and/or pharmacologically acceptable salts thereof, it is possible to more preferably exemplify:

3-hydroxy-2-(benzoylamino)propionic acid (Compound 2), 3-hydroxy-2-(methylbenzoylamino)propionic acid (Compounds 1, 3, 15), 3-acetoxy-2-(methylbenzoylamino)propionic acid (Compound 11), 2-(ethylbenzoylamino)-3-hydroxypropionic acid (Compound 7), 3-hydroxy-2-(methoxybenzoylamino)propionic acid (Compound 5), 2-(fluorobenzoylamino)-3-hydroxypropionic acid (Compound 4), 3-hydroxy-2-(trifluoromethylbenzoylamino)propionic acid (Compound 8), 3-hydroxy-2-(biphenylamino)propionic acid (Compound 14), 3-hydroxy-2-(naphthoylamino)propionic acid (Compound 10), 3-methoxy-2-(benzoylamino)propionic acid (Compound 16), 3-methoxy-2-(methylbenzoylamino)propionic acid (Compound 9), 3-hydroxy-2-(methylbenzoylamino)propionic acid methyl ester (Compound 6), 3-hydroxy-2-(methylbenzoylamino)propionic acid ethyl ester (Compound 17), 3-methoxy-2-(naphthoylamino)propionic acid (Compound 13), 3-hydroxy-2-(naphthoylamino)propionic acid methyl ester (Compound 12), isomers thereof, and/or pharmacologically acceptable salts thereof, it is possible to much more preferably exemplify:

3-hydroxy-2-(benzoylamino)propionic acid (Compound 2), 3-hydroxy-2-(methylbenzoylamino)propionic acid (Compounds 1, 3, 15), 2-(ethylbenzoylamino)-3-hydroxypropionic acid (Compound 7), 3-hydroxy-2-(methoxybenzoylamino)propionic acid (Compound 5), 2-(fluorobenzoylamino)-3-hydroxypropionic acid (Compound 4), 3-hydroxy-2-(trifluoromethylbenzoylamino)propionic acid (Compound 8), 3-methoxy-2-(benzoylamino)propionic acid (Compound 16), 3-methoxy-2-(methylbenzoylamino)propionic acid (Compound 9), 3-hydroxy-2-(methylbenzoylamino)propionic acid methyl ester (Compound 6), isomers thereof, and/or pharmacologically acceptable salts thereof, and it is possible to most preferably exemplify:

3-hydroxy-2-(methylbenzoylamino)propionic acid (Compound 1), 2-(fluorobenzoylamino)-3-hydroxypropionic acid (Compound 4), 3-hydroxy-2-(trifluoromethylbenzoylamino)propionic acid (Compound 8), isomers thereof, and/or pharmacologically acceptable salts thereof.

The compounds as described above have the excellent function to prevent or ameliorate (improve) the pigmentation. Further, the compounds are excellent in the solubility in the hydrophilic or lipophilic medium, and it is easy to produce or formulate the pharmaceutical preparation such as the external preparation for skin or the like. Further, the compounds are excellent in the stability in the pharmaceutical preparation and the skin retention, and the compounds exhibit the excellent effect to prevent or ameliorate (improve) the pigmentation.

The compounds represented by the general formulas (1) and (2) described above, the compounds defined in <2>, <3>, <4>, <6>, and <7> described above, the isomers thereof, and/or the pharmacologically acceptable salts thereof can be produced by performing, for example, the reactions of deprotection, coupling, and introduction of any protecting group in accordance with the following production method described in this specification and, for example, a method described, for example, in "Fundamental and Experiments for Peptide Synthesis (Maruzen)" by using a starting material of commercially available serine or serine derivative.

As for the compounds as described above, it is possible to use isomers thereof. The isomer means a stereoisomer such as an optical isomer. Further, each of the compounds represented by the general formulas (1) and (2) described above, the compounds defined in <2>, <3>, <4>, <6>, and <7> described above, the isomers thereof, and/or the pharmacologically acceptable salts thereof can exist in the form of a racemic substance which is a 1:1 mixture of (L) isomer and (D) isomer as well as a racemic mixture in which (L) isomer and (D) isomer exist at an arbitrary mixing ratio, in addition to the form of (L) isomer or (D) isomer which is optical isomer. The compounds represented by the general formulas (1) and (2) described above, the compounds defined in <2>, <3>, <4>, <6>, and <7> described above, the isomers thereof, and/or the pharmacologically acceptable salts thereof according to the present invention are usable in any one of the forms described above. However, it is preferable to use (L) isomer of the optical isomers in view of the efficacy of medicine or the safety.

The compounds as described above can be also used themselves as the prophylactic or ameliorating agent for pigmentation. Furthermore, they can be also used as salts after converting them into the form of salt by treating them together with pharmacologically acceptable acid or base. It is possible to preferably exemplify, for example, mineral acid salts including, for example, hydrochloride, sulfate, nitrate, phosphate, and carbonate; organic acid salts including, for example, maleate, fumarate, oxalate, citrate, lactate, tartrate, methanesulfonate, para-toluenesulfonate, and benzenesulfonate; alkali metal salts including, for example, sodium salt and potassium salt; alkaline earth metal salts including, for example, calcium salt and magnesium salt; organic amine salts including, for example, triethylamine salt, triethanolamine salt, ammonium salt, monoethanolamine salt, and piperidine salt; and basic amino acid salts including, for example, lysine salt and alginic acid salt.

The compounds represented by the general formulas (1) and (2) described above, the compounds defined in <2>, <3>, <4>, <6>, and <7> described above, the isomers thereof, and/or the pharmacologically acceptable salts thereof, which are thus obtained as described above, have the excellent prophylactic or ameliorating action for pigmentation. Therefore, they are useful as the active ingredients of the external preparation for skin. As for the pharmacological action of the active ingredient as described above, it is estimated that the melanin production is suppressed, for example, through inhibition of the melanocyte activation and the tyrosinase activity including, for example, inhibition of the tyrosinase enzymatic reaction, suppression of the tyrosinase gene expression, suppression of the tyrosinase protein production, and the tyrosinase-related protein degradation. Thus, it is possible to preferably exemplify the fact that the prophylactic or ameliorating action for pigmentation is provided.

As shown in Test Examples described later on, the compounds represented by the general formulas (1) and (2) described above, the compounds defined in <2>, <3>, <4>, <6>, and <7> described above, the isomers thereof, and/or the pharmacologically acceptable salts thereof have been confirmed to have the excellent action to suppress the activation of melanocyte in an in vitro evaluation system. It is considered that the compounds represented by the general formulas (1) and (2) described above, the compounds defined in <2>, <3>, <4>, <6>, and <7> described above, the isomers thereof, and/or the pharmacologically acceptable salts thereof exhibit the confirmed effect to suppress the pigmentation in an in vivo evaluation system by suppressing the melanin production on the basis of, for example, the action to suppress the activation of melanocyte as described above. That is, the compounds represented by the general formulas (1) and (2) described above, the compounds defined in <2>, <3>, <4>, <6>, and <7> described above, the isomers thereof, and/or the pharmacologically acceptable salts thereof are useful as the active ingredient of the prophylactic or ameliorating agent for pigmentation.

Any compound, which provides any action or function other than the prophylactic or ameliorating action or function for pigmentation, also exists in the compounds represented by the general formulas (1) and (2) described above, the compounds defined in <2>, <3>, <4>, <6>, and <7> described above, the isomers thereof, and/or the pharmacologically acceptable salts thereof. Any external preparation for skin, which contains the compound in order to express the action or function other than the prophylactic or ameliorating action or function for pigmentation, also belongs to the technical scope of the present invention. Because the external preparations to provide the action other than the prophylactic or ameliorating action or function for pigmentation utilizes the effect of the present invention, in case where the external preparations is principally aimed or intended to provide the prophylactic or ameliorating action or function for pigmentation as the action or function of the compounds represented by the general formulas (1) and (2) described above and/or the pharmacologically acceptable salts thereof. The external preparation for skin of the present invention is provided to prevent or ameliorate the pigmentation. The use of the external preparation for skin of the present invention is for preventing or ameliorating the pigmentation. The use for preventing or ameliorating the pigmentation includes the use for "skin whitening", "freckle amelioration" or the like, which principally aims at the object achieved by preventing or ameliorating the pigmentation.

<External Preparation for Skin of the Present Invention>

The external preparation for skin of the present invention is characterized in that the external preparation for skin contains the prophylactic or ameliorating agent for pigmentation consisting of any one of the compounds represented by the general formulas (1) and (2) described above, the compounds defined in <2>, <3>, <4>, <6>, and <7> described above, the isomers thereof, and/or the pharmacologically acceptable salts thereof.

In order to effectively exhibit the prophylactic or ameliorating action or function for pigmentation of the compounds represented by the general formulas (1) and (2), the compounds defined in <2>, <3>, <4>, <6>, and <7> described above, the isomers thereof, and/or the pharmacologically acceptable salts thereof, it is preferable to contain one or two or more of the species selected from the compounds represented by the general formulas (1) and (2), the compounds defined in <2>, <3>, <4>, <6>, and <7> described above, the isomers thereof, and/or the pharmacologically acceptable salts thereof in a total amount of 0.0001% by mass to 20% by mass, more preferably 0.001% by mass to 10% by mass, and much more preferably 0.005 to 5% by mass with respect to the total amount (gross amount) of the external preparation for skin. If the content with respect to the total amount (gross amount) of the external preparation for skin is less than 0.0001% by mass, the prophylactic or ameliorating action or function for pigmentation is lowered. On the other hand, even if an amount exceeding 20% by mass is used, the effect reaches the plateau. Therefore, it is preferable to adopt the content described above with respect to the total amount (gross amount) of the external preparation for skin.

Only one of the compounds represented by the general formulas (1) and (2) described above, the compounds defined in <2>, <3>, <4>, <6>, and <7> described above, the isomers thereof, and/or the pharmacologically acceptable salts thereof can be also contained in the external preparation for skin of the present invention. Alternatively, two or more of them can be also contained in combination in the external preparation for skin of the present invention.

The external preparation for skin of the present invention exhibits the effect for prevention or amelioration of those related to the abnormality relevant to the pigmentation, including, for example, for "prevention or amelioration of pigmentation", "skin whitening" and "freckle amelioration" by blending the compounds represented by the general formulas (1) and (2) described above, the compounds defined in <2>, <3>, <4>, <6>, and <7> described above, the isomers thereof, and/or the pharmacologically acceptable salts thereof.

In the external preparation for skin of the present invention, it is possible to contain any arbitrary component usually used for the cosmetic preparation, other than the essential components as described above. As for the arbitrary component as described above, it is possible to contain, for example, hydrocarbons including, for example, squalane, Vaseline, and microcrystalline wax; esters including, for example jojoba oil, carnauba wax, and octyldodecyl oleate; triglycerides including, for example, olive oil, beef tallow, and coconut oil; fatty acids including, for example, stearic acid, oleic acid, and retinoic acid; higher alcohols including, for example, oleyl alcohol, stearyl alcohol, and octyl dodecanol; anionic surfactants including, for example, sulfosuccinic acid ester and sodium polyoxyethylenealkylsulfate; amphoteric surfactants including, for example, alkyl betaine; cationic surfactants including, for example, dialkylammonium; nonionic surfactants including, for example, sorbitan fatty acid ester, fatty acid monoglyceride, polyoxyethylene adducts thereof, polyoxyethylene alkyl ether, and polyoxyethylene fatty acid ester; polyhydric alcohols including, for example polyethylene glycol, glycerol, and 1,3-butanediol; thickening/gelling agents; antioxidants; ultraviolet absorbing agents; coloring materials; antiseptics or preservatives; and powders. The external preparation for skin of the present invention can be produced without any difficulty by treating the components as described above in accordance with the ordinary method in addition to the prophylactic or ameliorating agent for pigmentation of the present invention.

The external preparation for skin of the present invention can be produced by treating the essential components and the arbitrary components as described above in accordance with the ordinary method, and processing the components, for example, into a lotion, a milky lotion, an essence, a cream, a pack cosmetic preparation, or a washing preparation. Any preparation form can be adopted provided that the preparation form can be applied to the skin. However, the active ingredient permeates into the skin to exhibit the effect. Therefore, it is more preferable to use the preparation form which is conformable to the skin, including, for example, the lotion, the milky lotion, the cream, and the essence.

The present invention will be explained in more detail below as exemplified by Examples. However, it goes without saying that the present invention is not limited to only Examples as described below.

EXAMPLES

Production Example 1

Production of Compound 1

Step 1 Synthesis of p-Methylbenzoyl Chloride p-Toluic acid (100 g, 0.734 mol) (Tokyo Chemical Industry Co., Ltd.) and toluene (500 mL) (Wako Pure Chemical Industries, Ltd.) were placed into a sufficiently dried recovery flask (egg plant flask), and p-toluic acid was dissolved. Thionyl chloride (132.4 mL, 1.84 mol) (Wako Pure Chemical Industries, Ltd.) was added dropwise to this solution for 1 hour. After the dropwise addition, the solution was heated and refluxed for 2 hours. After the reaction, the temperature was cooled to room temperature, and then remaining thionyl chloride and remaining toluene were evaporated by using a rotary evaporator. Toluene (200 mL) was added to an obtained concentrate, and the concentrating operation was repeated twice. A finally obtained residue was dissolved in tetrahydrofuran (200 mL) (Wako Pure Chemical Industries, Ltd.), which was used in the next step.

[Step 2] Synthesis of N-(p-methylbenzoyl)-L-serine

L-Serine (100 g, 0.952 mol) (Wako Pure Chemical Industries, Ltd.), potassium carbonate (131.5 g, 0.952 mol) (Wako Pure Chemical Industries, Ltd.), and water 1 L were placed into a recovery flask (egg plant flask), followed by stirring vigorously. p-Methylbenzoyl chloride prepared in Step 1 was dissolved in tetrahydrofuran (Wako Pure Chemical Industries, Ltd.), which was added dropwise to this solution for 30 minutes. During this process, pH was maintained in the vicinity of 8 while additionally adding potassium carbonate. After the completion of the dropwise addition, the agitation was performed for 1 hour. The reaction solution was added to water 1 L which was prepared in a distinct vessel, and then pH was adjusted to not more than 3 with hydrochloric acid, followed by being cooled to 4° C. Precipitated crystals were filtrated, followed by being recrystallized with a mixed solvent of ethanol (Wako Pure Chemical Industries, Ltd.)/water=6/4. An objective substance was obtained in an amount of 106.0 g (yield: 64.7%).

$^1$H-NMR ($d_6$-DMSO): δ 2.36 (3H, s), 3.80 (2H, d), 4.47 (1H, q), 7.29 (2H, d), 7.80 (2H, d), 8.29 (1H, d).

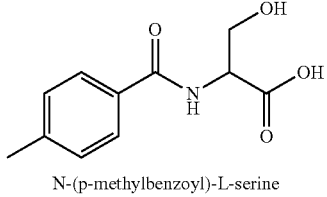

(Compound 1)

N-(p-methylbenzoyl)-L-serine

Production Example 2

Production of Compound 2

Compound 2 was synthesized in accordance with the same method as that used for Compound 1 described above by using benzoic acid and L-serine.

$^1$H-NMR (d$_6$-DMSO): δ 3.70 (2H, m), 4.23 (1H, q), 7.49 (3H, m), 7.88 (2H, d), 8.23 (1H, d).

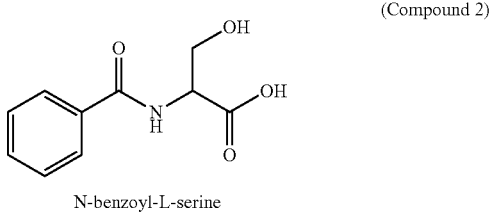 [SMILES: O=C(NC(CO)C(=O)O)c1ccccc1]

(Compound 2)

N-benzoyl-L-serine

Production Example 3

Production of Compound 3

Compound 3 was synthesized in accordance with the same method as that used for Compound 1 described above by using p-toluic acid and DL-serine.

$^1$H-NMR (d$_6$-DMSO): δ 2.36 (3H, s), 3.68 (2H, m), 4.19 (1H, m), 7.26 (2H, d), 7.76 (2H, d), 8.07 (1H, d).

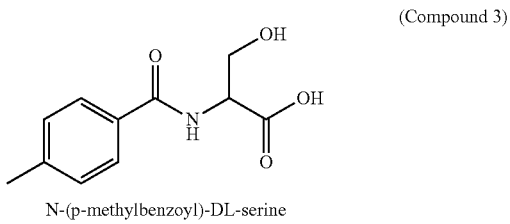 [SMILES: Cc1ccc(C(=O)NC(CO)C(=O)O)cc1]

(Compound 3)

N-(p-methylbenzoyl)-DL-serine

Production Example 4

Production of Compound 4

L-Serine (2.01 g, 19.1 mmol) (Peptide Institute, Inc.) and potassium carbonate (2.89 g, 20.9 mmol) (Wako Pure Chemical Industries, Ltd.) were weighed, and then water (10 mL) was added. A solution of p-fluorobenzoyl chloride (3.61 g, 22.8 mmol) (Wako Pure Chemical Industries, Ltd.)/tetrahydrofuran (10 mL) (Wako Pure Chemical Industries, Ltd.) was added dropwise for 9 minutes while being stirred and cooled with ice. The water bath was removed, and the temperature was returned to room temperature to perform the agitation for 43.5 hours. After that, tetrahydrofuran was evaporated under reduced pressure. Hydrochloric acid (4 mL) (Wako Pure Chemical Industries, Ltd.) was added while being stirred and cooled with ice, and pH was adjusted to not more than 2. Water (40 mL) was added, and the solid was obtained by filtration. The solid was sufficiently washed with water. After performing the drying for 4 hours under reduced pressure, the solid was dissolved in ethyl acetate (200 mL) (Wako Pure Chemical Industries, Ltd.), which was successively washed with a mixture solution of saturated saline solution (50 mL) and 5N hydrochloric acid (5 mL) (Wako Pure Chemical Industries, Ltd.) and saturated saline solution (100 mL×2). The organic layer was dried with anhydrous sodium sulfate (Wako Pure Chemical Industries, Ltd.), followed by being filtrated. The filtrate was concentrated under reduced pressure. tert-Butyl methyl ether (Tokyo Chemical Industry Co., Ltd.) was added to the concentrated residue, and undissolved matter was filtrated. Compound 4 was obtained in an amount of 1.65 g (yield: 38.0%).

$^1$H-NMR (CD$_3$OD): δ 4.01 (2H, m), 4.71 (1H, m), 7.22 (2H, m), 7.96 (2H, m).

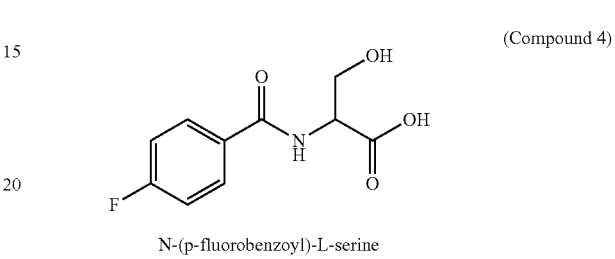

(Compound 4)

N-(p-fluorobenzoyl)-L-serine

Production Example 5

Production of Compound 5

Compound 5 was synthesized in accordance with the same method as that used for Compound 4 described above by using p-methoxybenzoyl chloride and L-serine.

$^1$H-NMR (CD$_3$OD): δ 3.87 (3H, s), 4.00 (2H, m), 4.71 (1H, m), 7.02 (2H, d), 7.88 (2H, d).

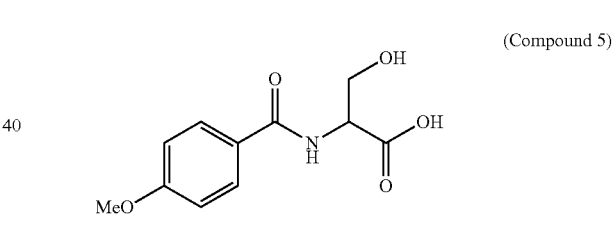

(Compound 5)

N-(p-methoxybenzoyl)-L-serine

Production Example 6

Production of Compound 6

L-Serine methyl ester hydrochloride (1.55 g, 9.96 mmol) (Tokyo Chemical Industry Co., Ltd.) was dispersed in dichloromethane (30 mL) (Wako Pure Chemical Industries, Ltd.), to which triethylamine (2.25 g, 22.2 mmol) (Wako Pure Chemical Industries, Ltd.) was added. A solution of p-methylbenzoyl chloride (1.78 g, 11.5 mmol) (Aldrich)/dichloromethane (5 mL) was added dropwise thereto for 3 minutes while being stirred and cooled with ice. The water bath was removed, and the temperature was returned to room temperature to perform the agitation for 6 hours. After that, the reaction solution was diluted with ethyl acetate (100 mL) (Wako Pure Chemical Industries, Ltd.), which was successively washed with saturated sodium hydrogencarbonate solution (30 mL), 1N hydrochloric acid (50 mL), and saturated saline solution (30 mL, 60 mL×2 L). The organic layer was dried with anhydrous sodium sulfate (Wako Pure Chemical Industries, Ltd.), followed by being filtrated. The filtrate was concentrated under reduced pressure. The residue was purified by silica gel column chromatography (n-hexane:ethyl acetate=1:2). Fractions containing the objective substance were collected, followed by being concentrated under reduced pressure. Compound 6 was obtained in an amount of 1.88 g (yield: 79.5%).

$^1$H-NMR (CDCl$_3$): δ 2.41 (3H, s), 2.58 (1H, brs), 3.83 (3H, s), 4.07 (2H, m), 4.88 (1H, m), 7.06 (1H, d), 7.25 (2H, d), 7.73 (2H, d).

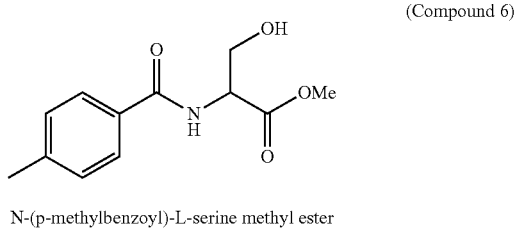 [SMILES: COC(=O)C(CO)NC(=O)c1ccc(C)cc1]

N-(p-methylbenzoyl)-L-serine methyl ester (Compound 6)

Production Example 7

Production of Compound 7

L-Serine (1.18 g, 11.2 mmol) (Peptide Institute, Inc.) and potassium carbonate (1.71 g, 12.4 mmol) (Wako Pure Chemical Industries, Ltd.) were weighed, and then water (5 mL) and tetrahydrofuran (5 mL) (Wako Pure Chemical Industries, Ltd.) were added. p-Ethylbenzoyl chloride (2.24 g, 13.3 mmol) (Wako Pure Chemical Industries, Ltd.) was added dropwise for 5 minutes while being stirred and cooled with ice. The water bath was removed, and the temperature was returned to room temperature to perform the agitation for 16 hours. After that, tetrahydrofuran was evaporated under reduced pressure. Hydrochloric acid (3 mL) (Wako Pure Chemical Industries, Ltd.) was added while being stirred and cooled with ice, and pH was adjusted to not more than 2. Water (20 mL) was added, and the solid was obtained by filtration. The solid was sufficiently washed with water. The solid was heated and dissolved in tert-butyl methyl ether (20 mL) (Tokyo Chemical Industry Co., Ltd.), which was thereafter washed with saturated saline solution (10 mL). The organic layer was dried with anhydrous sodium sulfate (Wako Pure Chemical Industries, Ltd.), followed by being filtrated. The filtrate was concentrated under reduced pressure. tert-Butyl methyl ether was added to the concentrated residue, and undissolved matter was filtrated. Compound 7 was obtained in an amount of 1.08 g (yield: 40.5%).

$^1$H-NMR (CD$_3$OD): δ 1.27 (3H, t), 2.73 (3H, q), 4.02 (2H, m), 4.72 (1H, m), 7.34 (2H, d), 7.82 (2H, d).

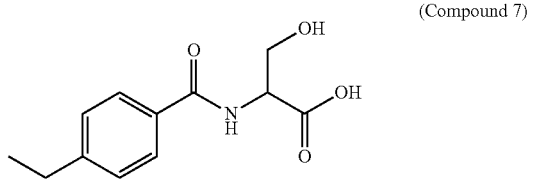

N-(p-ethylbenzoyl)-L-serine (Compound 7)

Production Example 8

Production of Compound 8

Compound 8 was synthesized in accordance with the same method as that used for Compound 7 described above by using p-(trifluoromethyl)benzoyl chloride and L-serine.

$^1$H-NMR (CD$_3$OD): δ 4.02 (2H, m), 4.74 (1H, m), 7.81 (2H, d), 8.07 (2H, d).

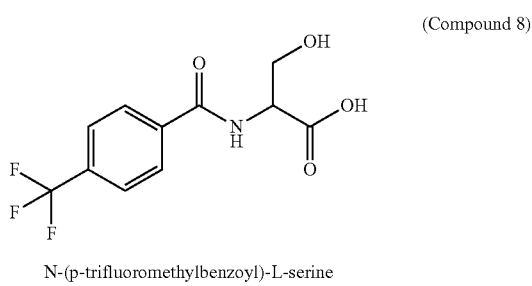 [SMILES: O=C(NC(CO)C(=O)O)c1ccc(C(F)(F)F)cc1]

N-(p-trifluoromethylbenzoyl)-L-serine (Compound 8)

Production Example 9

Production of Compound 9

Compound 9 was synthesized in accordance with the same method as that used for Compound 7 described above by using p-methylbenzoyl chloride and DL-O-methylserine.

$^1$H-NMR (d$_6$-DMSO): δ 2.36 (3H, s), 3.28 (3H, s), 3.71 (2H, m), 4.63 (1H, m), 7.28 (2H, d), 7.80 (2H, d), 8.49 (1H, d).

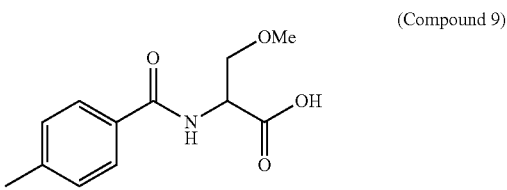

N-(p-methylbenzoyl)-DL-O-methylserine (Compound 9)

Production Example 10

Production of Compound 10

L-Serine (2.00 g, 19.0 mmol) (Peptide Institute, Inc.) was dispersed in tetrahydrofuran (19 mL) (Wako Pure Chemical Industries, Ltd.), and 2N aqueous sodium hydroxide solution (19 mL) was added while being stirred and cooled with ice. Subsequently, 2-naphthoyl chloride (3.64 g, 19.1 mmol) (Tokyo Chemical Industry Co., Ltd.) was added. The water bath was removed, and the temperature was returned to room temperature to perform the agitation for 16 hours. After that, tetrahydrofuran was evaporated under reduced pressure. Hydrochloric acid (4 mL) (Wako Pure Chemical Industries, Ltd.) was added while being stirred and cooled with ice, and pH was adjusted to not more than 2. The solid was obtained by filtration, which was sufficiently washed with water. tert-Butyl methyl ether (30 mL) (Tokyo Chemical Industry Co., Ltd.) was added, and undissolved matter was filtrated. This matter was thoroughly washed with tert-butyl methyl ether. Further, the matter was successively washed with tert-butyl methyl ether: ethyl acetate (=4:1) and n-hexane. Compound 10 was obtained in an amount of 2.92 g (yield: 59.2%).

$^1$H-NMR (CD$_3$OD): δ 4.04 (2H, m), 4.77 (1H, m), 7.59 (2H, m), 7.94 (4H, m), 8.46 (1H, s).

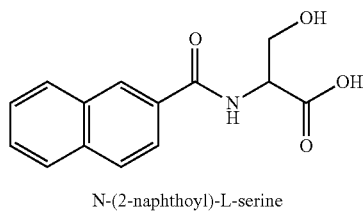

N-(2-naphthoyl)-L-serine (Compound 10)

Production Example 11

Production of Compound 11

Compound 11 was synthesized in accordance with the same method as that used for Compound 6 described above by using p-methylbenzoyl chloride and O-acetyl-L-serine hydrochloride.

$^1$H-NMR (d$_6$-DMSO): δ 1.91 (3H, s), 2.36 (3H, s), 4.28 (1H, dd), 4.46 (1H, dd), 4.71 (1H, m), 7.29 (2H, d), 7.78 (2H, d), 8.68 (1H, d).

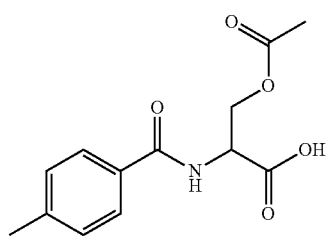

N-(p-methylbenzoyl)-O-acetyl-L-serine (Compound 11)

Production Example 12

Production of Compound 12

Compound 12 was synthesized in accordance with the same method as that used for Compound 6 described above by using 2-naphthoyl chloride and L-serine methyl ester hydrochloride.

$^1$H-NMR (d$_6$-DMSO): δ 3.67 (3H, s), 3.84 (2H, m), 4.61 (1H, m), 5.12 (1H, t), 7.62 (2H, m), 8.02 (4H, m), 8.53 (1H, s), 8.75 (1H, d).

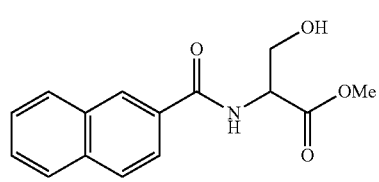

N-(2-naphthoyl)-L-serine methyl ester (Compound 12)

Production Example 13

Production of Compound 13

Compound 13 was synthesized in accordance with the same method as that used for Compound 4 described above by using 2-naphthoyl chloride and DL-O-methylserine.

$^1$H-NMR (d$_6$-DMSO): δ 3.31 (3H, s), 3.78 (2H, m), 4.72 (1H, m), 7.62 (2H, m), 8.01 (4H, m), 8.53 (1H, s), 8.78 (1H, d).

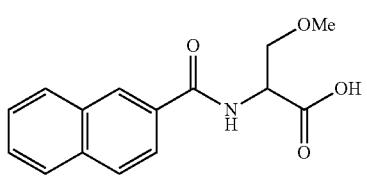

N-(2-naphthoyl)-DL-O-methylserine (Compound 13)

Production Example 14

Production of Compound 14

Compound 14 was synthesized in accordance with the same method as that used for Compound 4 described above by using 4-phenylbenzoyl chloride and L-serine.

$^1$H-NMR (CD$_3$OD): δ 4.03 (2H, m), 4.75 (1H, m), 7.45 (3H, m), 7.73 (4H, m), 7.99 (2H, s), 8.37 (1H, d).

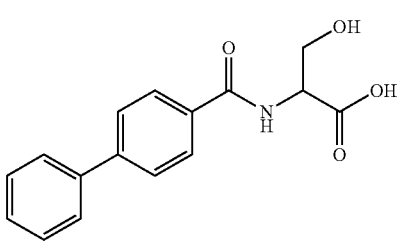

N-(p-phenylbenzoyl)-L-serine (Compound 14)

Production Example 15

Production of Compound 15

D-Serine (1.67 g, 15.9 mmol) (Tokyo Chemical Industry Co., Ltd.), water (9 mL), potassium carbonate (16.6 g, 16.6 mmol) (Wako Pure Chemical Industries, Ltd.), and tetrahydrofuran (9 mL) (Wako Pure Chemical Industries, Ltd.) were added to a recovery flask (egg plant flask), and p-methylbenzoyl chloride (2.59 g, 16.7 mmol) (Aldrich) was added dropwise for 2 minutes while being stirred and cooled with ice. The water bath was removed, and the temperature was returned to room temperature to perform the agitation for 26 hours. After that, hydrochloric acid (4 mL) (Wako Pure Chemical Industries, Ltd.) was added to the reaction solution, and pH was adjusted to not more than 2, followed by being stirred while being cooled with ice for 20 minutes. Precipitated crystals were collected by filtration, which were washed with water. The solid was dried under reduced pressure, and then 12 mL of ethyl acetate (Wako Pure Chemical Industries, Ltd.) was added to obtain undissolved matter by filtration.

The matter was washed with ethyl acetate. The matter was dried under reduced pressure for 24 hours, followed by being recrystallized with a mixture solvent of ethanol (Wako Pure Chemical Industries, Ltd.)/water=5/5. Compound 15 was obtained in an amount of 2.20 g (yield: 62.0%).

$^1$H-NMR (d$_6$-DMSO): δ 2.36 (3H, s), 3.79 (2H, d), 4.46 (1H, q), 7.29 (2H, d), 7.79 (2H, d), 8.28 (1H, d).

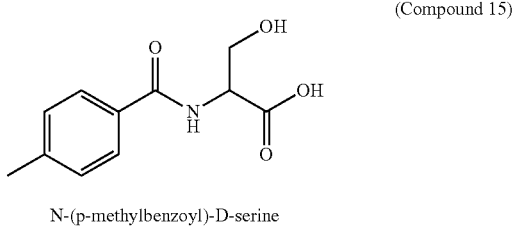 [SMILES: Cc1ccc(C(=O)NC(CO)C(=O)O)cc1]

(Compound 15)

N-(p-methylbenzoyl)-D-serine

Production Example 16

Production of Compound 16

Compound 16 was synthesized in accordance with the same method as that used for Compound 7 described above by using benzoyl chloride and DL-O-methylserine.

$^1$H-NMR (d$_6$-DMSO): δ 3.28 (3H, s), 3.72 (2H, m), 4.63 (1H, m), 7.62 (2H, m), 7.51 (3H, m), 7.88 (2H, s), 8.58 (1H, d).

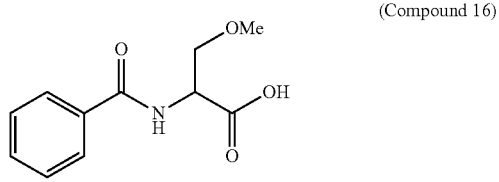

(Compound 16)

N-benzoyl-DL-O-methylserine

Production Example 17

Production of Compound 17

Compound 17 was synthesized in accordance with the same method as that used for Compound 6 described above by using p-methylbenzoyl chloride and L-serine ethyl ester hydrochloride.

$^1$H-NMR (CDCl$_3$): δ 1.33 (3H, t), 2.41 (3H, s), 2.70 (1H, t), 4.07 (2H, m), 4.29 (2H, q), 4.84 (1H, m), 7.09 (1H, d), 7.26 (2H, d), 7.73 (2H, d).

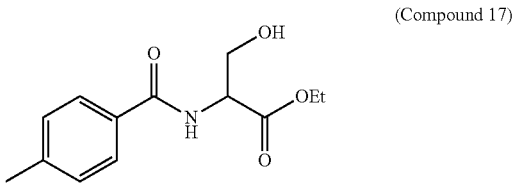

(Compound 17)

N-(p-methylbenzoyl)-L-serine ethyl ester

Test Example 1

Investigation of Ultraviolet B (UVB)-Induced Activation Inhibition Test Using Normal Human Melanocyte The suppressing effect of each of the compounds, which was exerted on the activation of melanocyte by the melanocyte activating factor produced and released from normal human keratinocyte by the ultraviolet B (UVB), was investigated by using the index of the cell proliferation function of normal human melanocyte.

Normal human keratinocyte cells (Kurabo Industries, Ltd.) were seeded by using Humedia-KG2 medium (Kurabo Industries, Ltd.) at a concentration of 10×10$^4$ cells/well in 24-well plate, followed by being cultured for 24 hours.

The compound to be evaluated was dissolved at a concentration of 100 mM in DMSO, which was diluted 1,000 times with Humedia-KG2 medium and used as a sample solution. As for the positive control group, tranexamic acid was dissolved at a concentration of 100 mM in DMSO, which was diluted 1,000 times with Humedia-KG2 medium and used as a positive control sample solution. As for the negative control group, DMSO was diluted 1,000 times with Humedia-KG2 medium, which was used as a negative control sample solution. A concentration, at which the cell proliferation of normal human melanocyte was not affected, was set for each of the compounds.

The medium of normal human keratinocyte was exchanged with Humedia-KG2 medium (sample solution) containing the compound at a predetermined concentration, and the cells were cultured for further 24 hours. After that, the medium was exchanged with PBS (phosphate buffered saline), and cells were irradiated with the ultraviolet B (UVB) at 5 mJ/cm$^2$ by using an ultraviolet lamp (FL20S•E-30/DMR, Toshiba Medical Supply Co., Ltd.) as a light source. After the ultraviolet radiation, PBS was exchanged with the sample solution. Cells were cultured for further 24 hours, and then the culture supernatant was collected.

Normal human melanocyte cells were seeded to 96-well plate by using a medium of Medium 254 (Kurabo Industries, Ltd.) so that the concentration was 3×10$^4$ cells/well, and the cultivation was performed for 24 hours. After that, the medium was exchanged with the culture supernatant collected from normal human keratinocyte, and the cells were cultured for further 24 hours. After the cultivation for 24 hours, the medium was exchanged with Humedia-KG2 medium containing 0.5 mg/mL of 3-(4,5-dimethyl-2-thiazoyl)-2,5-diphenyl-2H-tetrazolium bromide (MTT), and the cultivation was performed for 3 hours.

The formazan amount was determined by measuring the absorbances at 570 nm and 690 nm of cell lysate prepared with 2-propanol by means of a microplate reader (Benchmark Plus, Bio-Rad) and subtracting the absorbance at 690 nm from the absorbance at 570 nm.

The suppressing effect of each of the compounds on the melanocyte proliferation was represented by the percentage (%) as the formazan production ratio while the absorbance of the DMSO added group (negative control group) irradiated with the ultraviolet B (UVB) was assumed as 100.

It can be judged that the lower the production ratio of formazan is, the lower the melanocyte proliferation ratio is. Therefore, when the production ratio of formazan is lower, it is possible to judge that the suppressing activity of the compound to be evaluated is high with respect to the activation of melanocyte by the melanocyte activating factor produced and released by normal human keratinocyte.

TABLE 1

| Added compound | Ultraviolet B (UVB) (mJ/cm$^2$) | Melanocyte proliferation ratio Average (%) | Standard deviation (%) |
| --- | --- | --- | --- |
| DMSO | 0 | 47.9 | 3.40 |
| DMSO (negative control) | 5 | 100.0 | 5.82 |
| Tranexamic acid (positive control) | 5 | 82.0 | 6.19 |
| Compound 1 | 5 | 57.0 | 5.88 |
| Compound 2 | 5 | 60.9 | 6.37 |
| Compound 3 | 5 | 61.6 | 8.98 |
| Compound 4 | 5 | 55.3 | 2.20 |
| Compound 5 | 5 | 63.4 | 4.23 |
| Compound 7 | 5 | 65.1 | 8.80 |
| Compound 8 | 5 | 53.9 | 11.18 |
| Compound 9 | 5 | 62.3 | 3.66 |
| Compound 10 | 5 | 82.4 | 7.39 |
| Compound 11 | 5 | 71.8 | 6.60 |
| Compound 12 | 5 | 83.1 | 2.20 |
| Compound 13 | 5 | 80.3 | 6.34 |
| Compound 14 | 5 | 75.0 | 7.39 |
| Compound 15 | 5 | 60.2 | 4.60 |
| Compound 16 | 5 | 65.5 | 7.39 |
| Compound 17 | 5 | 73.6 | 4.76 |

The ratio of melanocyte proliferation shows the average and the standard deviation of three measurements.

According to the result shown in Table 1, all of the compounds exhibit the excellent suppressing effect, although the melanocyte activation suppressing activity involves any difference depending on the compound. Therefore, it has been revealed that all of the compounds have the excellent suppressing action or function with respect to the activation of melanocyte caused by the melanocyte activating factor produced and released from normal human keratinocyte.

Test Example 2

Investigation of Ultraviolet Ray-Induced Pigmentation Inhibition Test of Compound 1 Using Pigmented Guinea Pigs Skins of backs of eight pigmented guinea pigs were subjected to the hair removal and the hair shaving with electric hair clippers and shaver, and these sites were covered with black cloths each having four radiation windows of 2×2 cm in total disposed at two upper left and right positions and two lower left and right positions respectively. After that, the ultraviolet ray was radiated at 300 mJ/cm$^2$ by using FL20S•E30 lamp as the light source. This operation was repeatedly performed on 1st, 3rd, 5th, and 8th days of the test to induce the pigmentation at the four test sites. The compound to be evaluated (Compound 1) was dissolved and prepared in ethanol so that the concentration was 3% (w/v). Ethanol was applied as the solvent control group. The application of each of the compounds to be evaluated was started from the time of completion of the ultraviolet radiation on the 1st day of the test. Each of the compounds to be evaluated was applied in an amount of 30 μL once a day to the predetermined test sites, and this procedure was continuously carried out for 5 weeks (until 35th day of the test). The skin luminosity (Brightness) (L* value) was measured for each of the test sites by using a hue color difference meter (color analyzer) (CR-200, Konica Minolta Holdings Inc.) before the ultraviolet radiation on the application start day (on the 1st day of the test) and after 5 weeks (on the 36th day of the test) to determine the ΔL* value by subtracting the L* value before the ultraviolet radiation from the L* value on the 36th day of the test. That is, the stronger the degree of pigmentation is, the lower the L* value is. Therefore, it is possible to consider that the larger the ΔL* value is, the more suppressed the pigmentation is. Results are shown in Table 2.

TABLE 2

| Compound evaluated | Concentration | ΔL* value |
| --- | --- | --- |
| Solvent control group | — | −11.83 ± 0.78 |
| Compound 1 | 3% | −9.98 ± 0.71 |

ΔL* value indicates "average ± standard deviation" of 8 samples.

Example 1

Production Example 1 of External Preparation for Skin of the Present Invention A cosmetic preparation (lotion), which was the external preparation for skin of the present invention, was manufactured in accordance with a formulation shown in Table 3. That is, the formulation components were heated to 80° C., followed by being stirred, dissolved, and cooled while performing agitation to obtain the cosmetic preparation (Lotion 1). Similarly, a lotion of Comparative Example 1 in which the "pigmentation suppressing agent of the present invention (Compound 1)" was replaced with water and a lotion of Comparative Example 2 in which the "pigmentation suppressing agent of the present invention (Compound 1)" was replaced with arbutin were also manufactured.

TABLE 3

| Component | % by weight |
| --- | --- |
| Pigmentation suppressing agent of the present invention (Compound 1) | 3.0 |
| POE (60) hydrogenated castor oil | 0.1 |
| 1,3-Butanediol | 5.0 |
| Glycerin | 2.0 |
| Polyethylene glycol 400 | 3.0 |
| 1,2-Pentanediol | 3.0 |
| Xanthan gum | 0.1 |
| Potassium hydroxide | 0.85 |
| Methylparaben | 0.2 |
| Water | 82.75 |
| Total | 100 |

Example 2

Production Example 2 of External Preparation for Skin of the Present Invention A water-in-oil cream was prepared in accordance with a formulation shown in Table 4. That is, the components of A and B were heated to 80° C. respectively, and the components of B were gradually added to the components of A, followed by being emulsified. Particles were uniformized by using a homogenizer, followed by being stirred and cooled to obtain a cosmetic preparation (Cream 1).

TABLE 4

| Component | Parts by weight |
| --- | --- |
| A | |
| Sucrose fatty acid ester | 0.5 |
| Vaseline | 1.0 |

TABLE 4-continued

| Component | Parts by weight |
| --- | --- |
| Lanolin | 3.0 |
| Liquid paraffin | 8.0 |
| Low viscosity silicone | 30.0 |
| Stearyl alcohol | 0.5 |
| Stearic acid | 0.55 |
| Undecylenic acid monoglyceride | 2.0 |
| Organic modified bentonite | 2.0 |
| B | |
| 1,3-Butanediol | 5.0 |
| Glycerin | 20.0 |
| Compound 1 | 3.0 |
| Methylparaben | 0.2 |
| Water | 23.25 |
| Potassium hydroxide | 0.9 |
| Polyglucosyloxyethyl methacrylate (molecular weight: about 100,000) | 0.1 |

Example 3

Production Example of Cosmetic Preparation of the Present Invention

A cosmetic preparation (Milky lotion 1), which was the external preparation or composition for skin of the present invention, was manufactured in accordance with a formulation shown in Table 5. That is, the components of A, B, and C were heated to 80° C., and the components of C were gradually added to the components of B while being stirred, followed by being neutralized. After that, the components of A were gradually added while being stirred. Emulsified particles were uniformized by using Homo Mixer to obtain a milky lotion.

TABLE 5

| Component | Parts by weight |
| --- | --- |
| A | |
| Squalane | 10.0 |
| Sorbitan sesquistearate | 2.0 |
| Butylparaben | 0.1 |
| B | |
| 1,3-Butanediol | 5.0 |
| Xanthan gum | 0.1 |
| Pemulen TR-1 (acrylic acid-methacrylic acid alkyl copolymer) | 0.2 |
| Methylparaben | 0.1 |
| Compound 1 | 3.0 |
| Water | 48.55 |
| C | |
| Potassium hydroxide | 0.95 |
| Water | 30.0 |

Test Example 3

Ultraviolet Ray-Induced Pigmentation Inhibitory Effect of Lotion 1 in Human

The pigmentation suppressing effect was investigated by using Lotion 1 and the cosmetic preparations of Comparative Example 1 and Comparative Example 2. Sites of 1.5 cm×1.5 cm, which were disposed on an upper arm inner portion of each of panelists joined with spontaneity, were provided at two places while being divided into those disposed at upper and lower two parts in each and four places in total. The ultraviolet radiation in a minimum erythema dose (1 MED) was performed once a day, and the ultraviolet ray was radiated three times on continuous 3 days. Starting from the 1st day after the completion of the radiation, 50 μL of the sample was applied once a day for continuous 28 days. One site was an untreated site. After 24 hours after the completion of the application, the skin luminosity (Brightness) (L* value) was measured for each of the test sites by using a hue color difference meter (color analyzer) (CR-300, Konica Minolta Holdings Inc.) to calculate the ΔL* value with respect to the L value of the untreated site. The stronger the degree of pigmentation is, the lower the L* value is. Therefore, it is possible to judge that the larger the ΔL* value is, the more suppressed the pigmentation is. Results are shown in Table 6. Accordingly, it is appreciated that the cosmetic preparation (Lotion 1), which is the external preparation for skin of the present invention, has the excellent pigmentation suppressing effect. It is considered that this result is brought about by the pigmentation suppressing action of Compound 1 contained in Lotion 1 as described above.

TABLE 6

| Sample | ΔL* value |
| --- | --- |
| Lotion 1 | 0.87 |
| Comparative Example 1 | 0.15 |
| Comparative Example 2 | 0.65 |

INDUSTRIAL APPLICABILITY

The present invention can be applied to the external preparation for skin including, for example, the cosmetic preparation for skin whitening.

What is claimed is:

1. A method for preventing ameliorating pigmentation, comprising administering a compound represented by the following general formula (1), an isomer thereof, and/or a pharmacologically acceptable salt thereof to an individual in need thereof:

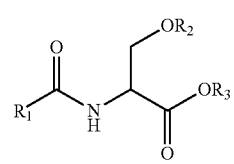

(1)

wherein:
  $R_1$ represents an unsubstituted aromatic group or an aromatic group having any substituent;
  $R_2$ represents a hydrogen atom, a linear chain or branched chain alkyl group having a number of carbon atom or atoms of 1 to 4, or an acyl group having a linear or branched alkyl chain having a number of carbon atom or atoms of 1 to 4; and
  $R_3$ represents a hydrogen atom or a linear chain or branched chain alkyl group having a number of carbon atom or atoms of 1 to 4.

2. The method according to claim 1, wherein in the general formula (1);
  $R_1$ is the unsubstituted aromatic group or the aromatic group having the substituent which is a linear chain or branched chain alkyl group having a number of carbon atom or atoms of 1 to 6, an alkoxy group having a linear or branched alkyl chain having a number of carbon atom or atoms of 1 to 6, an alkylamino group having a linear or branched alkyl chain or chains having a number of carbon atom or atoms of 1 to 6, an acyl group having a linear or branched alkyl chain having a number of carbon atom or atoms of 1 to 6, an ester group having a linear or branched alkyl chain having a number of carbon atom or atoms of 1 to 6, a halogen atom, a halogenated alkyl group, a hydroxy group, or an amino group;

$R_2$ is a hydrogen atom, a methyl group, an ethyl group, an n-propyl group, an isopropyl group, an n-butyl group, an isobutyl group, a tert-butyl group, an acetyl group, a propionyl group, or a butyryl group; and $R_3$ is a hydrogen atom, a methyl group, an ethyl group, an n-propyl group, an isopropyl group, an n-butyl group, an isobutyl group, or a tert-butyl group.

3. The method according to claim 2, wherein in the general formula (1);

$R_1$ is an unsubstituted phenyl, naphthyl, or biphenyl group or a phenyl, naphthyl, or biphenyl group having the substituent which is a linear chain or branched chain alkyl group having a number of carbon atom or atoms of 1 to 6, an alkoxy group having a linear or branched alkyl chain having a number of carbon atom or atoms of 1 to 6, an alkylamino group having a linear or branched alkyl chain or chains having a number of carbon atom or atoms of 1 to 6, an acyl group having a linear or branched alkyl chain having a number of carbon atom or atoms of 1 to 6, an ester group having a linear or branched alkyl chain having a number of carbon atom or atoms of 1 to 6, a halogen atom, a halogenated alkyl group, a hydroxy group, or an amino group;

$R_2$ is a hydrogen atom, a methyl group, or an acetyl group; and $R_3$ is a hydrogen atom, a methyl group, or an ethyl group.

4. The method according to claim 1, wherein the compound represented by the general formula (1) is N-benzoyl-serine, N-(p-methylbenzoyl)serine, N-(p-ethylbenzoyl)serine, N-(p-methoxybenzoyl)serine, N-(p-fluorobenzoyl)serine, N-(p-trifluoromethylbenzoyl)serine, N-(2-naphthoyl)serine, N-(4-phenylbenzoyl)serine, N-(p-methylbenzoyl)serine methyl ester, N-(p-methylbenzoyl)serine ethyl ester, N-(2-naphthoyl)serine methyl ester, N-benzoyl-O-methylserine, N-(p-methylbenzoyl)-O-methylserine, N-(p-methylbenzoyl)-O-acetylserine, N-(2-naphthoyl)-O-methylserine, an isomer thereof, and/or a pharmacologically acceptable salt thereof.

5. The method according to claim 2, wherein the compound represented by the general formula (1) is N-benzoyl-serine, N-(p-methylbenzoyl)serine, N-(p-ethylbenzoyl)serine, N-(p-methoxybenzoyl)serine, N-(p-fluorobenzoyl)serine, N-(p-trifluoromethylbenzoyl)serine, N-(2-naphthoyl)serine, N-(4-phenylbenzoyl)serine, N-(p-methylbenzoyl)serine methyl ester, N-(p-methylbenzoyl)serine ethyl ester, N-(2-naphthoyl)serine methyl ester, N-benzoyl-O-methylserine, N-(p-methylbenzoyl)-O-methylserine, N-(p-methylbenzoyl)-O-acetylserine, N-(2-naphthoyl)-O-methylserine, an isomer thereof, and/or a pharmacologically acceptable salt thereof.

6. The method according to claim 3, wherein the compound represented by the general formula (1) is N-benzoyl-serine, N-(p-methylbenzoyl)serine, N-(p-ethylbenzoyl)serine, N-(p-methoxybenzoyl)serine, N-(p-fluorobenzoyl)serine, N-(p-trifluoromethylbenzoyl)serine, N-(2-naphthoyl)serine, N-(4-phenylbenzoyl)serine, N-(p-methylbenzoyl)serine methyl ester, N-(p-methylbenzoyl)serine ethyl ester, N-(2-naphthoyl)serine methyl ester, N-benzoyl-O-methylserine, N-(p-methylbenzoyl)-O-methylserine, N-(p-methylbenzoyl)-O-acetylserine, N-(2-naphthoyl)-O-methylserine, an isomer thereof, and/or a pharmacologically acceptable salt thereof.

\* \* \* \* \*